(12) United States Patent
van der Krieken et al.

(10) Patent No.: US 10,342,228 B2
(45) Date of Patent: *Jul. 9, 2019

(54) POLYELECTROLYTE COMPLEXES FOR BIOCIDE ENHANCEMENT

(71) Applicant: Ceradis B.V., Wageningen (NL)

(72) Inventors: Wilhelmus Maria van der Krieken, Wageningen (NL); Wilhelmus Bernardus Hendrikus Rutten, Wageningen (NL); Christiaan Gerardus Johannes Maria Jans, Wageningen (NL)

(73) Assignee: CERADIS B.V., Wageningen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/495,384

(22) Filed: Apr. 24, 2017

(65) Prior Publication Data

US 2017/0303532 A1    Oct. 26, 2017

Related U.S. Application Data

(63) Continuation of application No. 14/382,949, filed as application No. PCT/NL2013/050143 on Mar. 5, 2013, now Pat. No. 9,635,855.

(30) Foreign Application Priority Data

Mar. 5, 2012 (EP) .................................. 12158136
Jun. 8, 2012 (EP) .................................. 12171345

(51) Int. Cl.
| | | |
|---|---|---|
| A01N 25/10 | (2006.01) | |
| A01N 25/24 | (2006.01) | |
| A01N 43/90 | (2006.01) | |
| A01N 41/04 | (2006.01) | |
| A01N 43/08 | (2006.01) | |

(52) U.S. Cl.
CPC .............. *A01N 25/10* (2013.01); *A01N 25/24* (2013.01); *A01N 41/04* (2013.01); *A01N 43/08* (2013.01); *A01N 43/90* (2013.01)

(58) Field of Classification Search
None
See application file for complete search history.

(56) References Cited

U.S. PATENT DOCUMENTS

| | | | |
|---|---|---|---|
| 4,148,891 A | 4/1979 | Smink | |
| 4,245,432 A | 1/1981 | Dannelly | |
| 5,578,598 A | 11/1996 | Abe et al. | |
| 8,337,923 B2 | 12/2012 | Coyne et al. | |
| 9,635,855 B2 | 5/2017 | van der Krieken et al. | |
| 2007/0065547 A1 | 3/2007 | Coyne et al. | |
| 2007/0085055 A1 | 4/2007 | Sikes et al. | |
| 2007/0104836 A1 | 5/2007 | Zhao et al. | |
| 2008/0254078 A1 | 10/2008 | Kauper et al. | |
| 2009/0117195 A1 | 5/2009 | Kauper et al. | |
| 2015/0038442 A1 | 2/2015 | van der Krieken et al. | |
| 2016/0192643 A1 | 7/2016 | Stark et al. | |
| 2016/0213051 A1 | 7/2016 | Stork et al. | |

FOREIGN PATENT DOCUMENTS

| | | | | |
|---|---|---|---|---|
| CN | 102120514 | * | 7/2001 | |
| CN | 101911944 A | | 12/2010 | |
| EP | 0865738 A1 | | 9/1998 | |
| FR | 2252056 | | 6/1975 | |
| JP | 09041271 | * | 2/1997 | |
| WO | 1995/008918 | | 4/1995 | |
| WO | 2004/0105491 A1 | | 12/2004 | |
| WO | 2008/009657 A2 | | 1/2008 | |
| WO | 2009077613 | | 6/2009 | |
| WO | 2010035118 A1 | | 4/2010 | |
| WO | WO-2011086196 A1 | * | 7/2011 | ........... A61K 9/1676 |
| WO | 2011123290 | | 10/2011 | |
| WO | 2011123297 | | 10/2011 | |
| WO | WO-2012036550 A1 | * | 3/2012 | ......... B01D 67/0079 |
| WO | 2012101256 A1 | | 8/2012 | |
| WO | 2013133706 A1 | | 9/2013 | |
| WO | 2015034359 A2 | | 3/2015 | |
| WO | 2015034360 A1 | | 3/2015 | |

OTHER PUBLICATIONS

International Search Report from corresponding International Application No. PCT/NL2013/050143 dated May 14, 2013.
Fredheim et al., "Polyelectrolyte Complexes: Interactions Between Lignosulfonate and Chitosan," Biomacromolecules, 4:232-239 (2003).
Wang et al., "Preparation of Lignosulfonate-Chitosan Polyelectrolyte Complex," Advanced Materials Research, vol. 197-198:1249-1252 (2011).
Thobunluepop, "The Inhibitory Effect of the Various Seed Coating Substances Against Rice Seed Borne Fungi and Their Shelf-Life During Storage," Pakistan Journal of Biological Sciences, 12:1102-1110 (2009).
Thobunluepop et al., "The Perspective Effects of Various Seed Coating Substances on Rice Seed Variety Khao Dawk Mali 105 Storability I," Pakistan Journal of Biological Sciences, 11:2291-2299 (2008).
Thobunluepop et al., "The Perspective Effects of Various Seed Coating Substances on Rice Seed Variety Khao Dawk Mali 105 Storability II," Pakistan Journal of Biological Sciences, 12:574-581 (2009).

(Continued)

*Primary Examiner* — Alton N Pryor
(74) *Attorney, Agent, or Firm* — McDermott Will & Emery LLP

(57) ABSTRACT

The invention relates to a composition comprising a polyelectrolyte complex of a polyanion and a polycation, and comprising at least one biocide. A preferred composition comprises lignosulfonate and chitosan, preferably in relative a amount of from 1:2 to 60:1 (w/w). The invention further relates to methods for generating a composition according to the invention, and to uses of a mixture according to the invention for protecting an agricultural plant or plant part against a pathogen.

27 Claims, No Drawings

(56) References Cited

OTHER PUBLICATIONS

Thobunluepop et al., "Physiological and Biochemical Evaluation of Rice Seed Storability with Different Seed Coating Techniques," International Journal of Agricultural Research, 4:169-184 (2009).
International Search Report from corresponding International Application No. PCT/NL2013/050144, dated May 8, 2013.
Merriam-Webster's Collegiate Dictionary, published 1998 by Merriam-Webster, Incorporated, p. 924.
Wang, C. et al., "Antifungal activity of eugenol against Botrytis cinera" Tropical Plant Pathology, 2010, pp. 137-143. vol. 35(3).
International Search Report from PCT Application No. PCT/NL2014/050607 dated Mar. 26, 2015.
International Search Report from PCT Application No. PCT/NL2014/050608 dated Nov. 28, 2014.
Tripathi et al., "Preparation and Physicochemical Evaluation of Chitosan/Poly (Vinyl Alcohol)/Pectintemary Film for Food-Packaging Applications,"Carbohydrate Polymers, 79:711-716 (2010).
Kim et al., "Chitosan-lignosulfonates sono-chemically prepared nanoparticles: Characterization and potential applications," Colloids Surf B Biointerfaces, 2013, 103:1-8.

* cited by examiner

POLYELECTROLYTE COMPLEXES FOR BIOCIDE ENHANCEMENT

RELATED APPLICATIONS

This application is a continuation of Ser. No. 14/382,949, filed Sep. 4, 2014, which is the U.S. National Stage of International Application No. PCT/NL2013/050143, filed Mar. 5, 2013, published in English, and claims the benefit of European Application Number 12158136.7, filed on Mar. 5, 2012 and European Application Number 12171345.7, filed on Jun. 8, 2012, the entire teachings of the above applications are incorporated herein by reference.

FIELD

The present invention relates to compositions comprising a biocide and a polyelectrolyte complex of a polyanion, such as lignosulfonate, and a polycation, such as chitosan. The invention further relates to compositions comprising a polyelectrolyte complex of a polyanion, such as lignosulfonate, and a polycation, such as chitosan. The invention further relates to methods for producing a composition of the invention and to methods of preventing, reducing and/or eliminating the presence of a pathogen on a plant or on one or more plant parts, comprising applying a composition of the invention to said plant or plant part.

INTRODUCTION

Plants are often threatened by various pathogenic micro-organisms like fungi, viruses and bacteria. To overcome the problem of infections with these micro-organisms, large quantities of anti-microbial compounds (in particular biocides, such as fungicides and bactericides) are applied. There is an ongoing concern about the possible negative impact of biocides on the environment and on human health. As a consequence, the demands with respect to sustainability of chemical pest control are continually increasing, as are the costs to bring new pesticides to the market.

In principle, reduced pressure of chemical biocides on the environment can be achieved by reduced quantities of chemicals applied for control of pathogenic micro-organisms. It is obvious that precise targeting and uniform distribution of the chemicals over the intended site of application is crucial to keep the input of chemicals to the environment as low as possible. This requires optimal formulation and optimal application procedures. Spray drift reduction (i.e. reduction of movement of pesticide through air to a site other than the intended site) is a well-known example of how on a macroscopic level substantial input reductions can be achieved without loss of efficacy. But also on a microscopic, molecular level targeting and distribution of the chemicals can be optimized, allowing significant lower input of absolute quantities of chemicals without loss of efficacy.

It is known that certain compounds of natural origin can protect plants against pathogenic micro-organisms. These natural biocides comprise organic substances derived from natural organisms (e.g. plant extracts) and anorganic compounds found in the natural environment (e.g. copperhydroxide or sulfur). The use of these natural biocides is becoming more and more preferable since governments aim for a reduction in the use of synthetic biocidal compounds.

It is therefore an objective of the present invention to provide a composition comprising plant protecting biocides that reduces the amount of biocide that is required to protect a plant against pathogenic micro-organisms.

SUMMARY OF THE INVENTION

The invention relates to a composition comprising a biocide and a polyelectrolyte complex of a polyanion, such as xanthan gum, alginate or a lignin-compound, and a polycation, such as poly-L-lysine and chitosan. Said composition is preferably used for protection of plants or plant parts against infections with a pathogen, including fungi. It was surprisingly found that said polyelectrolyte complex dramatically improved the protective effect of the biocide against a pathogen, in comparison with the same biocide without said polyelectrolyte complex. Without being bound by theory, said polyelectrolyte complex may provide improved, longer lasting, adherence of the biocide to the plant or plant part and/or the adherence to a pathogen, such as a fungus or an insect.

The polyelectrolyte complex of a polyanion and a polycation is an irreversible insoluble complex. This complex alone does not have biocidal efficacy. The polyelectrolyte complex has sticky properties and contains polar parts (charges) and apolar parts. The aromatic moieties in the complex may have affinity for the biocides which often also contain aromatic rings. In combination with the sticky character of the polyelectrolyte complex, the biocide will be optimally deposited and adhered to a plant or plant part.

The invention provides a composition, preferably a suspension, comprising at least one biocide and an insoluble polyelectrolyte complex of a polyanion and a polycation. Said polyanion is preferably selected from the group consisting of a natural polyanion such as xanthan gum, alginate, a lignin compound such as lignosulfonate, pectin, carrageenan, humic acid, fulvic acid, angico gum, gum Kondagogu, sodium alkyl naphtalene sulfonate (Morwet), poly-γ-glutamic acid, maleic starch half-ester, carboxymethyl cellulose, chondroitin sulphate, dextran sulphate, hyaluronic acid, and a synthetic polyanion such as poly(acrylic acid), polyphosphoric acid, and poly(L-lactide). Said polycation is preferably selected from the group consisting of poly-L-lysine, epsilon-poly-L-lysine, poly-L-arginine, chitosan oligosaccharide, and chitosan, whereby the lignin-compound and chitosan are in a relative amount of between 1:2 and 60:1 (w/w), more preferred between 2:1 and 30:1 (w/w), most preferred about 15:1 (w/w), even more preferred about 5:1 (w/w).

Said lignin-compound preferably comprises or is lignosulfonate, preferably a lignosulfonate salt such as, for example, calcium lignosulfonate, sodium lignosulfonate, potassium lignosulfonate, ammonium lignosulfonate, magnesium lignosulfonate etc.

The biocide in a composition according to the invention is preferably a fungicide.

A composition according to the invention can be a solid or, preferably, an aqueous composition, preferably a suspension.

The invention further provides a method for producing a composition according to the invention, comprising (a) providing an aqueous solution of a polyanion selected from the group consisting of a natural polyanion such as xanthan gum, alginate, a lignin compound such as lignosulfonate, pectin, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate, hyaluronic acid, and a synthetic polyanion such as poly(acrylic acid), polyphosphoric acid, and poly(L-lactide), wherein the concentration of said polyanion is from 0.1-60 w/v % or from 1-60 w/v %, (b) providing an aqueous acidic solution of a polycation selected from the group consisting of poly-L-lysine, epsilon-poly-L-lysine, poly-L-arginine, chitosan oligosaccharide, and chitosan, wherein the concentration of said polycation is from 0.1-10 w/v % or from 1-10 w/v % and the pH is below pH-5.5, (c) adding the solution of a polyanion to the solution of a polycation, whereafter the formed precipitate is crushed preferably milled in the presence of a dispersing agent and/or a wetting agent, followed by (d) adding a biocide. As an alternative, the biocide may be added to the solution of at least one of steps a-c. If required, an acid is added to the polycation-polyanion mixture to keep the pH of the mixture below pH=7, preferably below pH=5.5. The relative amount of a polyanion and a polycation in the composition is between 1:2 and 60:1 (w/w), more preferred between 2:1 and 30:1 (w/w), most preferred about 15:1 (w/w), even more preferred about 5:1. The final pH value my be adjusted to a pH value of between 3-12, more preferred between 5-9, most preferred between 6-7, depending on the biocide that is used, as is known to the skilled person.

A composition according to the invention is preferably used for the protection of a plant or a part of a plant against a pathogen. Therefore, the invention also provides the use of a composition comprising at least one biocide according to the invention, whereby the composition is sprayed over a plant or a part of a plant. Said composition is preferably used for protection against different forms of downy mildew, powdery mildew and *Botrytis*.

The invention further provides a method of protecting a plant or a plant part against a pathogen, comprising applying to said plant or on one or more plant parts a composition comprising at least one biocide according to the invention. Said composition is preferably diluted 2-1000 times, preferably about 200 times, with water to contain between 0.001 and 1% (w/v) of a biocide. The invention further provides a method of preventing, reducing and/or eliminating the presence of a pathogen on a plant or on one or more plant parts, comprising applying to said plant or plant part a composition comprising at least one biocide according to the invention, or a composition according to the invention that is diluted with water to contain between 0.001 and 20%, more preferred between 0.01 and 1% (w/v) of a biocide.

A preferred part of a plant is selected from seed, fruit and leaf. A most preferred part of a plant comprises or is a leaf. A further preferred part is a seed such as a vegetable seed, a bulb or a corn, or a post-harvest fruit, such as a citrus, for example an orange.

The invention further provides a drug delivery system comprising a drug and a polyelectrolyte complex of polyanion selected from the group consisting of a natural polyanion such as xanthan gum, alginate, a lignin compound such as lignosulfonate, pectin, carrageenan, humic acid, sodium alkyl naphtalene sulfonate, fulvic acid, angico gum, gum Kondagogu, poly-γ-glutamic acid, maleic starch half-ester, carboxymethyl cellulose, chondroitin sulphate, dextran sulphate, hyaluronic acid, and a synthetic polyanion such as poly(acrylic acid), polyphosphoric acid, and poly(L-lactide) and a polycation selected from the group consisting of poly-L-lysine, epsilon-poly-L-lysine, poly-L-arginine, chitosan oligosaccharide, and chitosan in a relative amount of between 1:2 and 300:1.

DETAILED DESCRIPTION

The term "polyion" refers to a molecule consisting of a plurality of charged groups that are linked to a common backbone. In the context of this application, the term "polycation" is interchangeable with the term "positively charged polyelectrolyte" and the term "polyanion" is interchangeable with the term "negatively charged polyelectrolyte".

The term "polyelectrolyte complex" refers to a complex of oppositely charged polyelectrolytes (a polyanion and a polycation) which form strong, but reversible electrostatic links, thus avoiding the use of covalent cross-linkers. The complex is not soluble.

The term "lignin compound" refers to a chemical compound that is derived from naturally occurring lignin or lignen by a process that includes sulphonation. The resulting sulfonic acids are strong acids and lignin compounds are therefore negatively charged at pH values below 7.

As used herein, the term "chitosan" refers to a linear polysaccharide composed of randomly distributed β-(1-4)-linked D-glucosamine (deacetylated unit) and N-acetyl-D-glucosamine (acetylated unit). Chitosan is produced by deacetylation of chitin. The term "chitosan" relates to chitosan, chitosan derivatives and mixtures of chitosan and chitosan derivatives.

The term "part of a plant" indicates a part of a plant including, but not limited to, pollen, ovule, leaf, root, flower, fruit, stem, bulb, corn, branch and seed.

In a preferred embodiment, the invention provides a composition comprising at least one biocide and a polyelectrolyte complex of a lignin-compound and chitosan. Lignin-compounds such as lignosulfonate form stable polyelectrolyte complexes with chitosan. A composition according to the invention may comprise a mixture of two or more lignin compounds and/or a mixture of two or more chitosan polymers.

A preferred lignin compound is selected from Kraft lignin, organosolv lignin and/or lignosulfonate.

A Kraft lignin is a polyphenolic product from the Kraft pulping process for the conversion of wood into wood pulp. Included are derivatives from Kraft lignin obtained by oxidation or other chemical modification as is known to the skilled person.

An organosolv lignin is a polyphenolic product from delignification processes using organic solvents. Included are derivatives from organosolv lignin obtained by oxidation or other chemical modification as is known to the skilled person.

Lignosulfonate (also termed lignosulphonate, lignosulfate, lignin sulfonate, ligninsulfonate, ligninsulfonic acid, lignosulfonic acid, lignosulfuric acid, or LST 7) is a water-soluble anionic polymer which is, for example, formed as a by-product in the sulphite pulping process.

Lignosulfonates generally have a wide molecular weight distribution, typically in the range of about 500 to about 150,000. Lignosulfonates may comprise different metal or ammonium ions as counter cations of the sulfonate groups such as, for example, copper, zinc, calcium, sodium, potassium, magnesium and aluminium. Suitable examples of lignosulfonates comprise sodium lignosulfonate (e.g. sold as BORRESPERSE NA®, Borregaard LignoTech Ltd, Germany), calcium lignosulfonate (e.g. sold as BORRESPERSE CA®, Borregaard LignoTech Ltd, Germany), ammonium lignosulfonate, potassium lignosulfonate, modified lignosulfonate, derivatives of lignosulfonate, or mixtures thereof. Modified lignosulfonates, and derivatives of lignosulfonates are described in U.S. Pat. Nos. 3,639,263, 3,923,532, 4,006,779, 4,017,475, 4,019,995, 4,069,217, 4,088,640, 4,133,385, 4,181,652, 4,186,242, 4,196,777, 4,219,471, 4,236,579, 4,249,606, 4,250,088, 4,267,886, 4,269,270, 4,293,342 4,336,189, 4,344,487, 4,594,168, 4,666,522, 4,786,438, 5,032,164, 5,075,402, 5,286,412, 5,401,718, 5,446,133, 5,981,433, 6,420,602, and 7,238,645, which are incorporated herein by reference.

A preferred lignin compound is lignosulfonate. A preferred lignosulfonate is copper-, zinc-, calcium-, sodium-, potassium-, ammonium-, magnesium- and/or aluminium-lignosulfonate, preferably calcium, sodium, potassium or ammonium lignosulfonate, most preferred calcium lignosulfonate.

The term chitosan relates to linear p-(1→4)-linked glucosamin and N-acetylglucosamin. It may be produced from chitin or its sodium salt (e.g. originating from shrimp) by treatment with aqueous sodium hydroxide at elevated temperatures, or by enzymatic treatment with, for example, a chitin deacetylase (EC 3.5.1.41). Further sources of chitin are fungi, including Basidiomycetes, Ascomycetes, and Phycomycetes, where it is a component of cell walls and structural membranes of mycelia, stalks, and spores. A most preferred chitosan is from fungi or derived from fungi.

Typically, deacetylation as determined by colloidal titration is from 50 to 99.9%, preferably from 70 to 99.8% and most preferably from 90 to 99.7%, as compared to chitin. Chitosan derivatives can be prepared by reactions at the amino group (e.g. by N-acylation, formation of N-alkylidene and N-arylidene derivatives, N-alkylation and N-arylation) or at hydroxy groups, as is known to the skilled person.

The polyelectrolyte complex comprises a polyanion, such as a lignin-compound, xanthan gum and alginate, and a polycation, such as chitosan, in a relative amount of between 1:2 and 60:1 (w/w), more preferred between 1:1 and 50:1, more preferred between 2:1 and 30:1, such as about 10:1; about 15:1, about 20:1, about 25:1 and about 30:1 (w/w). The relative amounts of polycation, preferably a lignin compound, and a polyanion, preferably chitosan, in a polyelectrolyte complex according to the invention is most preferred about 15:1, even more preferred about 5:1 (w/w).

A preferred composition comprises a biocide and a polyelectrolyte complex between a polycation, preferably chitosan, and a polyanion, preferably lignosulfonate. In a watery solution at a pH of about 4.5, polycations such as chitosan polymers are positively charged and the cationic amino groups on the glucosamine subunits can interact electrostatically with anionic groups (usually carboxylic acid groups) of polyanions such as lignosulfonate to form polyelectrolyte complexes. Many different polyanions of both natural origin, for example xanthan gum, alginate, pectin, a lignin compound such as lignosulfonate, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate, and hyaluronic acid, and synthetic origin, for example poly(acrylic acid), polyphosphoric acid, and poly(L-lactide) can be used to form polyelectrolyte complexes with a polycation, such as chitosan. Preferably, said polyanion is selected from the group consisting of xanthan gum, alginate and lignosulfonate. Most preferably, said polyanion comprises or is lignosulfonate.

Preferably, said polycation is selected from the group consisting of poly-L-lysine, epsilon-poly-L-lysine, poly-L-arginine, chitosan oligosaccharide, and chitosan. Most preferably, said polycation comprises or is chitosan. According to the present invention, a polyelectrolyte complex that is formed between a polyanion, preferably xanthan gum, alginate or lignosulfonate, and a polycation, preferably chitosan, in a relative amount of between 1:2 and 60:1 (w/w) improves the activity of a biocide, resulting in a reduction of the amount of biocide that is required to protect a plant or plant part against pathogenic micro-organisms. A particularly preferred embodiment provides a composition according to the invention comprising a polyelectrolyte complex of lignosulfonate and chitosan, and optionally at least one biocide.

The term "biocide" refers to a chemical substance capable of killing living organisms. Biocides are commonly used in medicine, agriculture, forestry, and in industry where they prevent the fouling of, for example, water, agricultural products including seed, and oil pipelines. A biocide can be a pesticide, including a fungicide, herbicide, insecticide, algicide, molluscicide, miticide and rodenticide; and/or an antimicrobial such as a germicide, antibiotic, antibacterial, antiviral, antifungal, antiprotozoal and/or antiparasite.

A preferred biocide in a composition according to the invention is a pesticidal agent including an antifungal compound, a herbicide, an insecticide, an acaricide, and/or a bactericide. A composition of the invention may also comprise two or more biocides, such as two or more fungicides, two or more herbicides, two or more insecticides, two or more acaricides, two or more bactericides, or combinations of, for example, at least one antifungal compound and at least one insecticide, at least one antifungal compound and at least one herbicide, at least one antifungal compound and at least one acaricide, at least one antifungal compound and at least one bactericide, at least one herbicide and at least one insecticide, at least one herbicide and at least one acaricide, at least one herbicide and at least one bactericide, at least one insecticide and at least one acaricide, at least one insecticide and at least one bactericide, and at least one acaricide and at least one bactericide. Some biocides have a wide range of target organisms, as is known to the skilled person, and are therefore include in more than one subgroup of biocides. A biocide is preferably present in a concentration of between 0.1 and 90 w/v %, more preferred between 1 and 70 w/v %, more preferred between 10 and 50 w/v %.

TABLE 1

Overview post-harvest fungicides

| Product name | Active ingredient | Company | Crop |
| --- | --- | --- | --- |
| Penbotec | pyrimethanil | PaceInternational | Citrus, pome fruit |
| Graduate | fludioxonil | PaceInternational | Citrus |
| Fungaflor | imazalil | PaceInternational | Citrus |
| Shield-Brite | thiabendazole | PaceInternational | Citrus, pome fruit |
| SOPP Soap | sodium ortho-phenylphenate | PaceInternational | Citrus |
| ecoFOG | pyrimethanil (fogging suitable) | PaceInternational | Pome |
| ScholarTM | fludioxonil | PaceInternational | Stone fruit, pome fruit, kiwi and yam |
| Philabuster | 200 g/l imazalil; 200 g/l pyrimethanil | BASF | Pear |
| Pristine | pyraclostrobin & boscalid | BASF | Grapes, berries, stone fruit, pome fruit, tree nuts, carrots as well as onions and other bulb vegetables |
| Bavistine | carbendazim | BASF | Fruit |
| Diabolo | imazalil | Certis | Potato |

A preferred antifungal compound or fungicide is a post harvest fungicide selected from Table 1, 2-phenylphenol; 8-hydroxyquinoline sulphate; acibenzolar-5-methyl; actinovate; aldimorph; amidoflumet; ampropylfos; ampropylfos-potassium; andoprim; anilazine; azoxystrobin; benalaxyl; benodanil; benomyl (methyl 1-(butylcarbamoyl)benzimidazol-2-ylcarbamate); benthiavalicarb-isopropyl; benzamacril; benzamacril-isobutyl; bilanafos; binapacryl; biphenyl; blasticidin-S; boscalid; bupirimate; buthiobate; butylamine; calcium polysulphide; capsimycin; captafol; captan (N-(trichloromethylthio)cyclohex-4-ene-1,2-dicarboximide); carbendazim; carboxin; carpropamid; carvone; chinomethionat; chlobenthiazone; chlorfenazole; chloroneb; chlorothalonil; chlozolinate; cis-1-(4-chlorophenyl)-2-(1H-1,2,4-triazol-1-yl)-cycloheptanol; clozylacon; a conazole fungicide such as, for example, (RS)-1-(β-allyloxy-2,4-dichlorophenethyl)imidazole (imazalil; Janssen Pharmaceutica NV, Belgium) and N-propyl-N-[2-(2,4,6-trichlorophenoxy)ethyl] imidazole-1-carboxamide (prochloraz); cyazofamid; cyflufenamid; cymoxanil; cyprodinil; cyprofuram; Dagger G; debacarb; dichlofluanid; dichlone; dichlorophen; diclocymet; diclomezine; dicloran; diethofencarb; diflumetorim; dimethirimol; dimethomorph; dimoxystrobin; dinocap; diphenylamine; dipyrithione; ditalimfos; dithianon; dodine; drazoxolon; edifenphos; ethaboxam; ethirimol; etridiazole; famoxadone; fenamidone; fenapanil; fenfuram; fenhexamid; fenitropan; fenoxanil; fenpiclonil; fenpropidin; fenpropimorph; ferbam; fluazinam (3-chlor-N-(3-chloro-5-trifluoromethyl-2-pyridyl)-α,α,α-trifluoro-2,6-dinitro-p-toluidine); flubenzimine; fludioxonil; flumetover; flumorph; fluoromide; fluoxastrobin; flurprimidol; flusulfamide; flutolanil; folpet (N-(trichloromethylthio)phthalimide); fosetyl-A1; fosetyl-sodium; fuberidazole; furalaxyl; furametpyr; furcarbanil; furmecyclox; guazatine; hexachlorobenzene; hymexazol; iminoctadine triacetate; iminoctadine tris(albesilate); iodocarb; iprobenfos; iprodione; iprovalicarb; irumamycin; isoprothiolane; isovaledione; kasugamycin; kresoxim-methyl; mancozeb; maneb; meferimzone; mepanipyrim; mepronil; metalaxyl; metalaxyl-M; methasulfocarb; methfiroxam; methyl 1-(2,3-dihydro-2,2-dimethyl-1H-inden-1-yl)-1H-imidazole-5-carboxylate; methyl 2-[[[cyclopropyl[(4-methoxyphenyl)imino]methyl]thio]-methyl]-.alpha-a.-(methoxymethylene)benzeneacetate; methyl 2-[2-[3-(4-chlorophenyl)-1-methyl-allylideneaminooxymethyl]phenyl]-3-meth-oxyacrylate; metiram; metominostrobin; metrafenone; metsulfovax; mildiomycin; monopotassium carbonate; myclozolin; N-(3-ethyl-3,5,5-trimethylcyclohexyl)-3-formylamino-2-hydroxybenzamide; N-(6-methoxy-3-pyridinyl)cyclopropanecarboxamide; N-butyl-8-(1,1-dimethylethyl)-1-oxaspiro[4.5]decan-3-amine; folpetnitrothal-isopropyl; noviflumuron; ofurace; orysastrobin; oxadixyl; oxolinic acid; oxycarboxin; oxyfenthiin; pencycuron; penthiopyrad; phosdiphen; phthalide; picobenzamid; picoxystrobin; piperalin; polyoxins; polyoxorim; procymidone; propamocarb; propanosine-sodium; propineb; proquinazid; pyraclostrobin; pyrazophos; pyrimethanil; pyroquilon; pyroxyfur; pyrrolnitrine; quinconazole; quinoxyfen; quintozene; silthiofam; sodium tetrathiocarbonate; spiroxamine; sulphur; tecloftalam; tecnazene; tetcyclacis; thiazole fungicide such as, for example, 2-(thiazol-4-yl)benzimidazole (thiabendazole; e.g. the commercial product TECTO® Flowable SC of Syngenta, USA), thicyofen; thifluzamide; thiophanate-methyl; thiram; tiadinil; tioxymid; tolclofos-methyl; tolylfluanid; triazbutil; triazoxide; tricyclamide; tricyclazole; tridemorph; trifloxystrobin; validamycin A; vinclozolin; zineb; ziram; zoxamide; (2S)—N-[2-4-[[3-(4-chlorophenyl)-2-propynyl)oxy]-3-methoxyphenyl]ethyl]-3-met-hyl-2-[(methylsulphonyl)amino]butanamide; 1-(1-naphthalenyl)-1H-pyrrole-2,5-dione; 2,3,5,6-tetrachloro-4-(methylsulphonyl)pyridine; 2,4-dihydro-5-methoxy-2-methyl-4-[[[[1-[3-(trifluoromethyl)phenyl]-ethyli-dene]amino]oxy]methyl]phenyl]-3H-1,2,3-triazol-3-one; 2-amino-4-methyl-N-phenyl-5-thiazolecarboxamide; 2-chloro-N-(2,3-dihydro-1,1,3-trimethyl-1H-inden-4-yl)-3-pyridinecarboxam-ide; 3,4,5-trichloro-2,6-pyridinedicarbonitrile; 3-[(3-bromo-6-fluoro-2-methyl-1H-indol-1-yl)sulphonyl]-N,N-dimethyl-1H-1,-2,4-triazole-1-sulphonamide; and copper salts such as Bordeaux mixture (CuSO4.3Cu(OH)2.3CaSO4); copper hydroxide; copper naphthenate; copper oxychloride ((CuCl2.3Cu(OH)2), tribasic copper sulphate (CuSO4.3Cu(OH)2); cufraneb; cuprous oxide; mancopper; oxine-copper A most preferred fungicide is folpet. A composition of the invention may also comprise two or more fungicides, such as, for example, folpet and copper hydroxide, folpet and a strobilurin type of fungicides like azoxystrobin, folpet and a triazole type of fungicides like cyproconazole, folpet and a succinate dehydrogenase inhibitor type of fungicides like boscalid, folpet and pthalimide/pthalonitrile type of fungicides like chlorothalonil, folpet and captan, folpet and benzimidazole type of fungicides like thiabendazole, folpet and carbamate type of fungicides like propamocarb, folpet and carboxamide type of fungicides like fenoxanil, folpet and dicarboxamide type of fungicides like iprodione, folpet and dithiocarbamate type of fungicides like Mancozeb, folpet and inorganic type of fungicides like copperhydroxide, folpet and morpholine type of fungicides like dimethamorph, folpet and organophosphate type of fungicides like fosetyl, folpet and azole type of fungicides like prothioconazole, folpet and phenylamide type of fungicides like metalaxyl, folpet and fungicides not belonging to a specific group of fungicides like fludioxynil.

A further preferred biocide is an insecticide and/or acaricide. Preferred insecticides include imidacloprid (commercial product: ADMIRE®, Bayer) Bacillus thuringiensis (commercial product: TUREX®, Certis USA), teflubenzuron (commercial product: NOMOLT®, BASF), pymetrozine (commercial product: PLENUM®, Syngenta) and acetamiprid (Commercial product: GAZELLE®, Certis Europe), ACTELLIC® Syngenta, Switzerland), Pyrethroids (commercial product BAYGON® (Bayer), bifenazate (e.g. Uniroyal), dichlorvos (e.g. Amvac Chemical Corporation), imidacloprid (e.g. Bayer), fenamiphos (e.g. Mobay Chemical Corporation), orange oil, D-limonene, oxamyl (e.g. Dupont) and sulfur-based insecticides. A most preferred insecticide is pirimiphos-methyl (commercial product ACTELLIC®, Syngenta, Switzerland). A composition of the invention may also comprise two or more insecticides.

Preferred acaricides include chlofentezine (commercial product: APOLLO®, Makhteshim), acequinocyl (commercial product: KAMEMYTE®, Arysta), spirodiclofen (commercial product: ENVIDOR®, Bayer CropScience), bifenazate (commercial product: FLORAMITE®, Certis Europe) and fenbutatinoxide (commercial product: TORQUE L®, BASF). A most preferred acaricide is spirodiclofen. A composition of the invention may also comprise two or more acaricides.

A further preferred insecticide/acaricide is a carbamate, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metamsodium, methiocarb, methomyl, metolcarb, oxamyl, pirimicarb, promecarb, propoxur, thiodicarb, thiofanox, trimethacarb, XMC, xylylcarb, triazamate; an organophosphate, for example acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-S-methyl, demeton-S-methylsulphon, dialifos, diazinon, dichlofenthion, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion; a sodium channel modulator/voltage-dependent sodium channel blocker, such as a pyrethroid, for example acrinathrin, allethrin (d-cis-trans, d-trans), beta-cyfluthrin, bifenthrin, bioallethrin, bioallethrin-S cyclopentyl isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta.), cyphenothrin, deltamethrin, empenthrin (IR isomer), esfenvalerate, etofenprox, fenfluthrin, fenpropathrin, fenpyrithrin, fenvalerate, flubrocythrinate, flucythrinate, flufenprox, flumethrin, fluvalinate, flibfenprox, gamma-cyhalothrin, imiprothrin, kadethrin, lambda-cyhalothrin, metofluthrin, permethrin (cis-, trans-), phenothrin (IR trans-isomer), prallethrin, profluthrin, protrifenbute, pyresmethrin, resmethrin, RU 15525, silafluofen, tau-fluvalinate, tefluthrin, terallethrin, tetramethrin (IR isomer), tralomethrin, transfluthrin, ZXI 8901; an oxadiazine, for example indoxacarb; an acetylcholine receptor agonists/antagonists; a chloronicotinyl, for example clothianidin, dinotefuran, imidacloprid, nitenpyram, nithiazine, thiacloprid, thiamethoxam; a nicotine such as bensultap, cartap; an organochlorine, for example camphechlor, chlordane, endosulfan, gamma-HCH, HCH, heptachlor, lindane, methoxychlor, a fiproles, for example acetoprole, ethiprole, fipronil, pyrafluprole, pyriprole, vaniliprole; a mectin, for example avermectin, emamectin, emamectin-benzoate, ivermectin, milbemycin; a juvenile hormone mimetics, for example diofenolan, epofenonane, fenoxycarb, hydroprene, kinoprene, methoprene, pyriproxifen, triprene; an ecdyson agonists/disruptors such as a diacylhydrazines, for example chromafenozide, halofenozide, methoxyfenozide, tebufenozide; benzoylureas, for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron an organotin, for example azocyclotin, cyhexatin, fenbutatin-oxide; a pyrrole, for example chlorfenapyr; a dinitrophenol, for example binapacryl, dinobuton, dinocap, a tetronic acid, for example spirodiclofen, spiromesifen; a tetramic acid, for example spirotetramat and 3-(2,5-dimethylphenyl)-8-methoxy-2-oxo-1-azaspiro[4.5]dec-3-en-4-yl ethyl carbonate; a carboxamide, for example flonicamid; a benzoic acid dicarboxamide, for example flubendiamide; azadirachtin, a fumigant, for example aluminium phosphide, methyl bromide, sulphuryl fluoride; an antifeedant, for example cryolite, flonicamid, pymetrozine; a mite growth inhibitor, for example clofentezine, etoxazole, hexythiazox; amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, and/or verbutin.

A further preferred biocide is a bactericide, for example bronopol, dichlorophen, nitrapyrin, nickel dimethyldithiocarbamate, kasugamycin, octhilinon, furancarboxylic acid, oxytetracyclin, probenazole, streptomycin, tecloftalam, and copper salts. Preferred bactericides include compounds such as copper salts (e.g. copper hydroxide, copper oxychloride, copper sulfate and Bordeaux mixture), sophorolipid which is a glycolipid that is produced by yeasts such as *Candida bombicola, Candida apicola*, and *Wickerhamiella domerciae* and is composed of a dimeric sugar linked with a glycosidic bond to a hydroxyl fatty acid, streptomycin, the commercial product CITRICIDAL® (Bio/Chem Research) and validamycin. A most preferred bactericide is copper hydroxide. A composition of the invention may also comprise two or more bactericides.

Some of the indicated compounds have more than one activity. For example, copper salts (e.g. copper hydroxide) have bactericide and fungicide activities. The activities of the individual compounds are known to the skilled person. In addition, handbooks and websites (e.g. www.frac.info/frac) are available to determine the activity or activities of a compound.

A most preferred biocide in a composition according to the invention is a fungicide, preferably folpet and/or an insecticide, preferably limonene. A further preferred biocide is a mixture of two or more active ingredients. A preferred mixture comprises folpet and limonene or folpet and a sophorolipid. Said mixture preferably comprises folpet and limonene or a sophorolipid in ratio of between 30:1 and 1:30 (w/w), preferably in a ratio of about 1:1 (w/w).

A preferred biocide according to the invention is a natural biocide. The term natural biocide comprises micro-organisms and virusses, feromones, extracts from plants and/or animals, and other substances such as, for example, minerals. Preferred plant extracts are or comprise Sage extract (=extract of *Salvia officinalis*), extract of *Reynoutria sachalinensis* (Giant Knotweed), extract of *Verticillium alboatrum*, extract of *Bacillus thuringiensis* subsp. *Kurstaki*, extract of Lecanicillium muscarium, laminarin, lactoperoxidase, azadirachtin, harpin, chitosan, nisin, pythium extract (and other fungal extracts). Preferred other substances include salicylic acid, castor oil, carvon, cedar oil, cinnamon and cinnamon oil, citric acid, citronella and citronella oil, cloves and clove oil, corn gluten meal, corn oil, cottonseed oil, eugenol, garlic and garlic oil, geraniol, geranium oil, lauryl sulphate, lemongrass oil, linseed oil, malic acid, mint and mint oil, peppermint and peppermint oil, 2-phenethyl propionate (2-phenylethyl propionate), sorbate such as potassium sorbate, putrescent whole egg solids, rosemary and limonene, sesame and sesame oil, sodium chloride, sodium lauryl sulphate, soybean oil, thyme and thyme oil, white pepper, a sulfur-based compound, a copper-based compound, carbamates such as sodiumdimethyldithiocarbamaat, quaternary ammonium compounds, benzyl-C12-16-alkyldimethyl, chlorides, sodium dichloroisocyanurate, calcium hypochlorite, ethanol, 2-propanol, didecyldimethylammonium chloride, ethylene oxide, sodium dichloroisocyanurate, trichloroisocyanic acid, peracetic acid, hydrogen peroxide, sodium-p-tolueensulfonchloramide, glutaraldehyde, N-(3-aminopropyl)-N-dodecylpropane-1,3-diamine, lactic acid, sodium hypochlorite, decanoic acid, octanoic acid, bronopol, imizalil, 1,2-benzisothiazole-3(2H)-on, dichlofluanide, propiconazole, permethrin, boric acid, flufenoxuron, 1,3-dichloro-5,5-dimethylhydantoine, 1,3-dichloro-5-ethyl-5-methylimidazolidine, 2,2-dibroom-2-cyanacetamide, bromo chloro-5,5-dimethylimidazolidine, difenacoum, difethialon, bromadiolon, flocoumafen, dichloorvos, diflubenzuron, cyromazin, bifenthrin, cyromazin, imidacloprid, deltamethrin, permethrin, tetramethrin, d-fenothrin, cyfluthrin, piperonylbutoxide, pyrethrine, alfa-cypermethrin, magnesiumfosfide, piperonylbutoxide, N,N-diethyl-m-toluamide, p-menthane-3,8-diol, cybutryne, cymoxanil, mancozeb, captan, linuron, prochloraz, glyfosate, nicosulfuron, folpet, chloridazon, milbemectin, metamitron, metsulfuron-methyl, gibberellic acid, azoxystrobin, spirotetramat, abamectin, indolyl butyric acid, teflubenzuron and/or limonene, and/or mixtures thereof.

A composition according to the invention preferably further comprises at least one additional compound selected from the group consisting of a sticking agent, a preservative, a stabilizer, a wax, an antioxidant, an anti-foam-forming agent, a thickening agent, a spray oil, an UV, protectant, an anti-freezing agent, a dispersing agent, and a flow additive.

Said sticking agent is preferably selected from latex based products like PROLONG® (Holland Fyto B.V., The Netherlands) and BOND® (Loveland Industries Ltd), pinolene/terpene based products like NU-FILM® (Hygrotech Saad) and SPRAY-FAST® (Mandops), long chain polysaccharides like gellan gum, guar gum, succinoglycan gum (RHEOZAN®; Rhodia) and xanthan gum, or a hydrated magnesium-aluminum silicate, for example attapulgite, (Attagel®; BASF). Alternatively, the sticking agent may be a polymer or co-polymer from a type of polymer such as polyacrylate and polyethylene e.g. NEOCRYL® (DSM, The Netherlands). A composition of the invention may also comprise two or more different sticking agents. A sticking agent is preferably present in an amount of between 0 to up to 20% (w/v), more preferred between 0.1 to up to 10% (w/v), more preferred between 1 to up to 5% (w/v), more preferred about 3% (w/v).

A preservative is preferably selected from weak acid preservatives such as sorbic acid, lactic acid, benzoic acid, propionic acid, citric acid, acetic acid, or an alkali metal or alkali earth metal salt thereof; inorganic acids such as hydrochloric acid; imidazoles such as imazalil or any antifungal compound known in the art as a preservative for food products, crop protection or after harvest treatment of fruits, vegetables or cereals; ethyl parabenzoate; borax; calcium bisulfite; calcium disodium EDTA; dehydroacetic acid; isothiazoles (e.g. KATHON® (Rohm and Haas); a quaternary ammonium salt such as, for example, 1-(3-chloroallyl)-3,5,7-triaza-1-azoniaadamantane chloride (CTAC), and antimicrobials capable of preventing bacterial growth in the composition. A preferred preservative is a quaternary ammonium salt, preferably CTAC stabilized with sodium bicarbonate (Dowicil® 75). A further preferred preservative is Kathon™, which is preferably present in a concentration of about 0.04 gram/liter. A composition of the invention may also comprise two or more different biocides. A composition of the invention may also comprise two or more different preservatives. A preservative is preferably present in an amount between 0 to up to 20% (w/v), more preferred between 0.01 to up to 10% (w/v), more preferred between 0.1 to up to 5% (w/v), more preferred about 0.5% (w/v).

A stabilizer, when present, is preferably selected from xanthan gum, agar, succinoglycan gum (Rheozan), alginic acid, alginate, a hydrated magnesium-aluminum silicate, for example attapulgite, (Attagel®; BASF), calcium lactobionate, carrageenan, OptiXan-D®; gellan gum, and guar gum. A composition of the invention may also comprise two or more different stabilizing agents. A stabilizer is preferably present in an amount of between 0 to up to 10% (w/v), more preferred between 0.01 to up to 5% (w/v), more preferred between 0.05 to up to 0.5% (w/v), more preferred about 0.05% (w/v).

A wax, when present, is preferably a natural or synthetic wax selected from bee wax, carnauba wax, andelilla wax, ouricouri wax, sugarcane wax, retamo wax, Chinese wax, jojoba oil, paraffin wax, esparto wax, Montan wax, candelilla wax, whale spermaceti, lanolin, and ethylene glycol diesters or triesters of long-chain fatty acids (C18-C36). A wax is preferably present in an amount of between 0 to up to 10% (w/v), more preferred between 0.01 to up to 5% (w/v), more preferred between 0.05 to up to 0.5% (w/v), more preferred about 0.1% (w/v).

An antioxidant, when present, is preferably selected from amino acids (e.g. glycine, histidine, tyrosine, tryptophan) and their derivatives, imidazole (e.g. urocanic acid) and derivatives, vitamin C and derivatives (such as ascorbylpalmitate and ascorbyltetraisopalmitate, Mg-ascorbylphosphate, Na-ascorbylphosphate, ascorbyl-acetate), tocopherol and derivates (such as vitamin-E-acetate), mixtures of vitamin E, vitamin A and derivatives (vitamin-A-palmitate and -acetate) as well as coniferyl benzoate, rutinic acid and derivatives, □-glycosylrutin, ferulic acid, furfurylideneglucitol, carnosine, butylhydroxytoluene, butylhydroxyanisole, and trihydroxybutyrophenone. A composition of the invention may also comprise two or more different antioxidants. An anti-oxidant is preferably present in an amount between 0 to of up to 20% (w/v), more preferred between 0.1 to up to 10% (w/v), more preferred between 1 to up to 5% (w/v), more preferred about 3% (w/v).

An anti-foam forming agent, when present, is preferably selected from polymethylsiloxane, simethicone octanol, and silicone oils. The composition of the invention may also comprise two or more different anti-foam forming agents. An anti-foam agent is preferably present in an amount of between 0 to up to 10% (w/v), more preferred between 0.05 to up to 5% (w/v), more preferred between 0.1 to up to 1% (w/v), more preferred about 0.05% (w/v).

A thickening agent, when present, is preferably selected from agar, alginic acid, alginate, carrageenan, gellan gum, xanthan gum, succinoglycan gum, guar gum, acetylated distarch adipate, acetylated oxidised starch, arabinogalactan, ethyl cellulose, methyl cellulose, locust bean gum, starch sodium octenylsuccinate, and triethyl citrate. A composition of the invention may also comprise two or more different thickening agents. A thickening agent is preferably present in an amount of between 0 to up to 10% (w/v), more preferred between 0.01 to up to 5% (w/v), more preferred between 0.02 to up to 1% (w/v), more preferred about 0.05% (w/v).

An UV-protector or UV absorbent, when present, is preferably selected from sulphonated tannins, titaniumdioxide, lignosulfonates, and related compounds. An UV-protector is preferably present in amount of between 0.1 and 10% (w/v).

A composition according to the invention optionally further comprises an additional compound selected from a spray oil, for example, a mineral oil such as BANOLE®.

In addition, a dispersing or wetting agent known to a skilled person such as, for example, Morwet® D425, lignin sulphonate, an alkylpolysaccharide, an styrene acrylic polymer, an acrylic co-polymer, and ethoxylated tristyrenephenol phosphate, for example polyethoxylated fosforic acid, and/or a wetting agent such as di-octylsuccinate, polyoxy-ethylene/polypropylene and tri-stearyl sulphonate/phosphate, is preferably present.

A further preferred composition according to the invention comprises folpet and a wax, a sophorolipid and a wax, or a combination of folpet, a sophorolipid and a wax. Said mixture preferably comprises folpet and a sophorolipid in ratio of between 30:1 and 1:30 (w/w), preferably in a ratio of about 1:1 (w/w).

The invention further provides a method for producing a composition according to the invention, comprising (a) providing an aqueous solution of a polyanion selected from the group consisting of a natural polyanion such as xanthan gum, alginate, a lignin compound such as lignosulfonate, pectin, carrageenan, humic acid, fulvic acid, angico gum, gum Kondagogu, poly-γ-glutamic acid, maleic starch half-ester, carboxymethyl cellulose, chondroitin sulphate, dextran sulphate, hyaluronic acid, and a synthetic polycation such as poly(acrylic acid), polyphosphoric acid, and poly (L-lactide), wherein the concentration of said polyanion is from about 0.1-70 w/v %, from about 1-70 w/v %, (b) providing an aqueous acidic solution of a polycation selected from the group consisting of poly-L-lysine, epsilon-poly-L-lysine, poly-L-arginine and chitosan, wherein the concentration of said polycation is from about 0.1-10 w/iv %, from about 1-10 w/v % and the pH is below pH=5.5, (c) adding the solution of a polycation to the solution of a polyanion, or vice versa, whereby a precipitate is formed that is crushed, for example by milling, preferably to an average particle size of between 0.2 and 5 micrometer, whereafter (d) a biocide is added. As an alternative, a biocide is added to the solution of at least one of steps a-c.

If required, an acid is added to the polycation-polyanion mixture to keep the pH of the mixture below pH=7. A preferred acidic polycation, preferably chitosan, solution comprises lactate, phosphorous acid, hydrochloric acid, fumaric acid, and/or ascorbic acid.

Said polyanion is preferably selected from the group consisting of xanthan gum, alginate and a lignin compound such as lignosulfonate. In a preferred embodiment, said polyanion comprises or is a lignin compound, most preferably lignosulfonate. Said polycation is preferably selected from the group consisting of poly-L-lysine, epsilon-poly-L-lysine, poly-L-arginine and chitosan. In a preferred embodiment, said polycation comprises or is chitosan.

As an alternative, a method for producing a composition according to the invention comprises (a) providing an aqueous solution of a polyanion, preferably a lignin compound, xanthan gum or alginate, wherein the concentration of said polyanion is from about 0.1-70 w/v %, from about 1-70 w/v %, (b) providing a polycation solution, preferably a chitosan solution, wherein the concentration of polycation is from about 0.1-10 w/v %, from about 1-10 w/v %, (c) adding the polycation solution to the solution of a polyanion or vice versa, while the pH of the mixture is kept below pH=5.5, and (d) adding a biocide to at least one of steps a-c.

An aqueous solution of a polyanion, such as a lignin compound, is preferably prepared by dissolving a polyanion, such as a lignin compound, preferably lignosulfonate, in an aqueous solution, preferably water.

A solution of a polycation, preferably chitosan, is preferably prepared by solubilising the polycation, preferably chitosan, in an aqueous acidic solution comprising, for example, lactate, hydrochloric acid, phosphorous acid and/or ascorbic acid. The amount of acid that is required to solubilise the polycation, preferably chitosan, depends on the polycation, as is known to the skilled person. For instance for solubilising chitosan, in general, about 6 ml 37% hcl is required to obtain a 10 gram in 1 liter chitosan solution in water. As an alternative, a polycation, preferably chitosan, is dissolved in an aqueous solution, preferably water, for example by gently shaking at 20-23° C. overnight. A salt, preferably NaCl, is preferably added at a concentration between 1 mM and 1 M, preferably about 100 mM.

A polyanion solution, preferably a lignosulfonate, xanthan gum, humic acid, or alginate solution, is preferably added drop wise to the solution comprising a polycation, preferably a chitosan compound. If required, the pH is kept below 5.5 by the addition of an acid, preferably hydrochloric acid, lactic acid, ascorbic acid, phosphorous acid, nonanoic acid or acetic acid. The pH is more preferably kept below 5.0, more preferably below 4.5 during the formation of a polyelectrolyte complex. The temperature is preferably between 0° C. and 100° C., more preferred between 10° C. and 60° C., more preferred ambient temperature (15-25° C.). The resulting mixture is preferably stirred during formation of the polyelectrolyte complex and the polyelectrolyte complex is preferably allowed to settle overnight.

It is preferred that a polyanion, preferably a lignosulfonate, xanthan gum, humic acid, or alginate, is added to a solution comprising a polycation, preferably a chitosan compound. If required, the pH is kept below 5.5 by the addition of an acid, preferably hydrochloric acid, lactic acid, ascorbic acid, phosphorous acid, nonanoic acid or acetic acid. The pH is more preferably kept below 5.0, more preferably below 4.5 during the formation of a polyelectrolyte complex. The temperature is preferably between 0° C. and 100° C., more preferred between 10° C. and 60° C., more preferred ambient temperature (15-25° C.). The resulting mixture is preferably stirred during formation of the polyelectrolyte complex and the polyelectrolyte complex is preferably allowed to settle overnight.

Following settlement of the ply-electrolyte complex, a dispergent and/or a wetting agent is preferably added and the precipitate is crushed, preferably by milling for example in a bead mill. The resultant concentrate may further comprise a sticking agent, a preservative, a stabilizer, a wax, an antioxidant, an anti-foam-forming agent, a thickening agent, a spray oil, an UV-protectant, an anti-freezing agent such as, for example monopropylene glycol, and a flow additive.

The invention further provides a use of a composition according to the invention for the protection of a plant or a part of a plant against a pathogen. Said composition preferably comprises at least one biocide. Said plant preferably is a vegetable, fruit or crop plant.

A composition according to the invention is a solid composition, for example a granule, or a liquid, preferably aqueous, composition, more preferably a suspension. Prior to use, a composition according to the invention comprising at least one biocide is preferably dissolved or dispersed in water or diluted with water to contain between 0.001 and 1 w/v % of a biocide. If required, a sticking agent is added to the diluted aqueous suspension. Said aqueous composition is used, for example, to control brown rot of peaches, powdery mildew of apples, gooseberries, hops, ornamentals, grapes, peaches, strawberries, and sugar beets, apple scab, gall mite on blackcurrant, peanut leafspot, mildew on roses, and mites on beans, carrots, lucerne, melons, and tomatoes. For this, the aqueous composition is preferably sprayed over a plant, or part thereof, for use as a biocide, preferably as a fungicide.

A composition according to the invention comprising a polyelectrolyte complex and at least one biocide is for instance in the form of a suspension concentrate (SC), water dispersible granules (WG), a wettable powder (WP), an emulsifiable concentrate (EC) a dispersion concentrate (DC), a dry powder seed treatment (OS), a water slurriable powder (WS), a suspo emulsion (SE), a flowable seed treatment (FS) or a water dispersible granule seed treatment (WG). Preferably, a composition of the invention is in the form of a suspension concentrate, or in the form of water dispersible granules. A "suspension concentrate" as used herein refers to a suspension of solid particles in a liquid intended for dilution with water prior to use. A "dispersion concentrate" as used herein refers to a dispersion of solid particles in a liquid intended for dilution with water prior to use. "Water dispersible granules" as used herein refer to a formulation in granule form which is dispersible in water forming a dispersion such as a suspension or solution. A "wettable powder" as used herein refers to a powder formulation intended to be mixed with water or another liquid prior to use. A "water slurriable powder" as used herein refers to a powder formulation that is made into a slurry in water prior to use.

Alternatively, a plant of part thereof is coated with an aqueous composition comprising at least one biocide according to the invention by submerging the plant or part thereof in the aqueous composition to protect the plant of part thereof against a pathogen. A preferred part of a plant that is coated with a composition according to the invention is a bulb, a corn, or a seed. A further preferred part of a plant that is coated with a composition according to the invention is a fruit such as, for example, a citrus fruit such as orange, mandarin and lime, a pome fruit such as apple and pear, a stone fruit such as almond, apricot, cherry, damson, nectarine, tomato and watermelon; a tropical fruit such as mango, lychee and tangerine. A preferred fruit is a citrus fruit, such as orange.

A preferred part that is coated with a composition according to the invention is a post-harvest fruit, such as a citrus fruit such as orange, mandarin and lime, a pome fruit such as apple and pear, a stone fruit such as almond, apricot, cherry, damson, nectarine, tomato and watermelon; a tropical fruit such as mango, lychee and tangerine. A preferred post-harvest fruit is a citrus fruit, such as orange.

Said pathogen preferably is a fungus or an oomycete, esp. *Phytophthora* sp. or *Plasmopara viticola*. A preferred fungus is *botrytis* and/or *Penicillium* sp.

The invention further provides a method of protecting a plant against a pathogen, comprising applying to said plant, or on one or more plant parts, a composition according to the invention. Said composition is preferably dissolved or dispersed in water or diluted with water to contain between 0.001 and 1 w/v % of a biocide or a combination of biocides. A preferred composition for applying to a plant or a part of a plant comprises folpet and a wax, a sophorolipid and a wax, or a combination of folpet, sophorolipid and a wax.

The invention further provides a method of preventing, reducing and/or eliminating the presence of a pathogen on a plant or on one or more plant parts, comprising applying to said plant or plant part a composition according to the invention. A preferred plant part according to the invention is selected from seed, leaf and fruit such as, for example, a citrus fruit such as orange, mandarin and lime, a pome fruit such as apple and pear, a stone fruit such as almond, apricot, cherry, damson, nectarine, tomato and watermelon; a tropical fruit such as mango, lychee and tangerine. A preferred fruit is a citrus fruit, such as orange. A most preferred part is a post-harvest fruit.

The invention further provides a drug delivery system comprising a drug and a polyelectrolyte complex of a polyanion selected from the group consisting of a natural polyanion such as a lignin compound such as xanthan gum, alginate, lignosulfonate, pectin, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate, hyaluronic acid, and a synthetic polyanion such as poly(acrylic acid), polyphosphoric acid, and poly(L-lactide) and a polycation selected from the group consisting of poly-L-lysine, epsilon-poly-L-lysine, poly-L-arginine, chitosan oligosaccharide, and chitosan, in a relative amount of between 1:2 and 300:1. A chitosan based polyelectrolyte complexes exhibit favourable physicochemical properties with preservation of chitosan's biocompatible characteristics. These complexes are therefore good candidate excipient materials for the design of different types of dosage forms. For example, the chitosan-based complexes can be used as excipients in drug delivery systems such as nano- and microparticles, beads, fibers, sponges and matrix type tablets. Said drug delivery system can be used as a non immediate release dosage form selected from delayed release, sustained release, controlled release, prolonged release, and site specific release.

Said drug delivery system is preferably prepared by a method comprising (a) providing an polyanion or an aqueous solution of a polyanion selected from the group consisting of a natural polyanion such as xanthan gum, alginate, a lignin compound such as lignosulfonate, pectin, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate, hyaluronic acid, poly(acrylic acid), polyphosphoric acid, and poly(L-lactide), wherein the concentration of said polyanion is from about 0.1-60 w/v %, from about 1-60 w/v %, (b) providing a solution of a polycation selected from the group consisting of poly-L-lysine, epsilon-poly-L-lysine, poly-L-arginine, chitosan oligosaccharide, and chitosan, wherein the concentration of polycation is from about 0.1-10 w/v %, from about 1-10 w/v %, (c) adding the polyanion to the solution of polycation, or adding the solution of the polycation to the polyanion while the pH of the mixture is kept below pH=5.5 by addition of an acid, whereby a precipitate is formed that is crushed and (d) adding a drug to the solution of at least one of steps a-c.

Nanoparticles comprising a polyelectrolyte complex according to the invention, such as of a lignin-compound and chitosan, can be prepared by adding an aqueous solution of calcium chloride comprising a drug to a solution of a polyanion, preferably a lignin compound, while stirring. A polycation, preferably chitosan, solution is than added to the calcium polyanion pre-gel. The resultant opalescent suspension is than equilibrated overnight to allow nanoparticles to form with a uniform particle size.

A drug that is present in a drug delivery system according to the invention can be any agent which is preferably not immediately released after administration. Examples of active agents that are preferably released at a defined time after administration, for example in the early morning, are anti-asthmatics (e.g. bronchodilators), anti-emetics, cardiotonics, vasodilators, anti-vertigo and anti-meniere drugs, anti-ulceratives, corticosteroids such as prednisone, other anti inflammatory drugs, analgetics, anti-rheumatics, anti-arthritic drugs; anti-angina drugs; and anti-hypertensives, in addition, other compounds for which such formulations can be very useful to improve patient compliance comprise sedatives such as diazepam, antidepressants, and other CNS compounds. Other classes of agents that are preferably formulated in drug delivery system according to the invention are bioactive proteins, peptides, enzymes, vaccines and oligonucleotides. These types of compounds are often not resistant to the acidic environment of the stomach, and are therefore preferably released in the small and/or large intestine.

Yet another class of drugs that are preferably formulated in drug delivery system according to the invention is probiotic bacteria. Non-limiting examples of probiotic bacteria are *Bacillus coagulans* sp., *Bifidobacterium animalis*, *Bifidobacterium breve*, *Bifidobacterium infantis*, *Bifidobacterium longum*, *Lactobacillus acidophilus*, *Lactobacillus casei*, *Lactobacillus paracasei*, *Lactobacillus fortis*, *Lactobacillus johnsonii*, *Lactobacillus plantarum*, *Lactobacillus reuteri*, *Lactobacillus rhamnosus*, *Saccharomyces boulardii*, and mixtures thereof.

Some forms of chitosan, e.g. shrimp-derived chitosan, are generally recognized as save and have GRAS status. It is preferred that the polyanion, such as a lignin compound, and the polycation, such as chitosan, that are used in a drug delivery system according to the invention are sufficiently pure and are of pharmacological grade.

EXAMPLES

General

For all examples, the term 'CitoCaL' refers to the polyelectrolyte complex of Ca-lignosulfonate and chitosan Example 1

6 young grapevines (cv Merlot) per treatment were grown outside or under greenhouse cover (open tunnel) in pots. Plants were treated 4 times (7 days interval) with the indicated dose rate in a spray volume of 1000 l/ha until run-off. Four days after the 2nd fungicide application, 2 out of 6 plants were inoculated with *Plasmopara viticola*. These 2 plants served as a natural inoculum for the remaining 4 plants. Disease progression was assessed once a week.

Results

The results of experiments with Folpet and Captan 500SC are depicted in Tables 1 and 2.

TABLE 1

Effect of application of Folpet 500SC with and without CitoCal on of *Plasmopara viticola* infection on leafs of grapevine. Presented is the % of leaf area that was infected.

| Product | Dose rate | Infected leaf area days after infection | | |
|---|---|---|---|---|
| Folpet 500 SC | (L/ha) | 7 d | 14 d | 21 d |
| Standard Folpet | 0.5 | 42 | 59 | 61 |
| CitoCal* with Folpet | 0.5 | 30 | 36 | 39 |
| Standard Folpet | 2 | 29 | 38 | 46 |
| CitoCal with Folpet | 2 | 5 | 9 | 14 |

TABLE 2

Effect of application of Captan 500SC with and without CitoCal on *Plasmopara viticola* infection on leafs of grapevine. Presented is the % of leaf area infected.

| Product | Dose rate | Infected leaf area days after infection | | |
|---|---|---|---|---|
| Captan 500 SC | (L/ha) | 7 d | 14 d | 21 d |
| Standard | 0.5 | 39 | 50 | 66 |
| CitoCal | 0.5 | 21 | 30 | 35 |
| Standard | 2 | 35 | 40 | 46 |
| Citocal | 2 | 15 | 25 | 26 |

*CitoCal: polyelectrolyte complex of lignosulfonate and chitosan in a 5:1 (w/w) ratio.

Example 2

Materials and Methods

Tested fruit: apple from organic origin/SKAL certified. SKAL is a semi-governmental Dutch organization that controls organic production in the Netherlands.

Tested formulation: final concentration of 100 ppm natamycin in different formulation backgrounds (see also example 3 and table 4).

Used pathogen: *Botrytis cinerea* spore-suspension containing ~$10^5$ propagules (spores)/ml.

Treatments:

1) Mock (=formulation ingredients only)
2) Lignosulfonate (LS) and chitosan (CTS) polyelectrolyte complex (CitoCal) without active ingredient (a.i.)
3) LS+CTS without a.i.
4) LS without a.i.
5) CTS without a.i.
6) Mock+natamycin
7) CitoCal+natamycin
8) LS+CTS+natamycin
9) LS+natamycin
10) CTS+natamycin Application: Fruit peel was damaged with a cork borer, depth~0.5 cm into the fruit, 2 wounds per fruit. Three droplets of a freshly prepared spore suspension of *B. cinerea* (estimated $10^5$ spores/ml) were applied by pipette into each wound. Subsequently, the spore-suspension was allowed to air-dry for 4 hours. Treatments 1-10 were diluted 100 times in tap water and were applied to each wound after inoculation by airbrush until run-off (3 short bursts~20 cm distance of fruit surface).

All fruits were kept at room temperature (20° C.). Wounds were examined daily for 15 days or until the fruit was completely spoiled.

Replicates: All treatments (1-10) were performed on 5 individual pieces of fruit with 2 wounds each resulting in 10 wounds per treatment.

Observation: All wounds were inspected daily for visual symptoms of fruit rot and/or fungus growth.

Rot diameter (perpendicular) was measured at three succeeding days. The observations were ended when all wounds of the control formulations (1-5) showed maximal symptoms of fruit rot/and or fungal growth.

Results

The results are depicted in Table 3.

TABLE 3

| | Apple | | | |
|---|---|---|---|---|
| Product: | Average diameter (cm) of infected spot (n = 10) days after infection | | | |
| Natamycin | 2 | 5 | 6 | AUDPC* |
| Mock | 1.2 | 4.8 | 6.1 | 14.4 |
| Mock + CitoCal | 1 | 4.6 | 5.7 | 13.6 |
| Mock + LS + CTS | 1.1 | 4.7 | 6 | 13.9 |
| Mock + LS | 1.1 | 4.6 | 5.8 | 13.7 |
| Mock + CTS | 1 | 4.5 | 5.8 | 13.3 |
| Mock + natamycin | 0.3 | 1.6 | 2.4 | 4.8 |
| Mock + CitoCal + natamycin | 0.3 | 0.4 | 0.7 | 1.6 |
| Mock + LS + CTS + natamycin | 0.3 | 2.4 | 3.6 | 7.1 |
| Mock + LS + natamycin | 0.4 | 2.5 | 3.7 | 7.4 |
| Mock + CTS + natamycin | 0.4 | 3.5 | 4.9 | 9.9 |

*AUDPC: Area Under the Disease Progressive Curve

The sprayed mock formulation comprised 0.2 g/L sodiumdioctylsuccinate, 0.75 g/L sophorolipid, 0.55 g/L of a 2% xanthan and 0.01 g/L surfynol 104E Summary & Conclusion:

Phytotoxicity

Two days after inoculation, *Botrytis* fruit rot was observed on apples that were treated with a formulation that did not contain natamycin. Apples treated with natamycin did not show any symptoms.

Five and six days after inoculation, a clear difference was noticeable between apples treated with and without natamycin. *Botrytis* symptoms on apples not treated with natamycin was ~4.7 cm (5 dpi) and ~5.9 cm (6 dpi). Rot on apples treated with natamycin was clearly lower, especially the apples treated with CitoCal and natamycin. Interestingly, apples treated with natamycin+CaLS+CTS (non-polymer of CitoCal) was by far not as effective as polymeric CitoCal.

Example 3

Materials and Methods:

Tested Crop: banana fruit (SKAL certified; SKAL is a semi-governmental Dutch organization that controls organic production in the Netherlands).

Application: The fruit peel was damaged with a sterile nail, depth about 0.5 cm into the fruit, 2 wounds per fruit. Three droplets of a freshly prepared spore suspension of *Botrytis cinerea* ($10^5$ spores/ml) was applied by pipette into each wound. Subsequently, the applied spore-suspension was allowed to air-dry for 4 hours. Treatments 1-10 (see table 4) were applied to each wound after diluting 100 times in tap water by airbrush until run-off (3 short bursts at about 20 cm distance of fruit surface). All fruits were kept at room temperature (20° C.).

Treatments:

1) Adjuvants (Control)
2) Adjuvants plus Chitosan-Ca-Lignosulfonate polyelectrolyte complex (CitoCaL).
3) Adjuvants plus Chitosan and Lignosulfonate (no polyelectrolyte binding).
4) Adjuvants plus Ca-lignosulfonate
5) Adjuvants plus chitosan
6) Adjuvants plus natamycin
7) Adjuvants plus CitoCaLplus Natamycin
8) Adjuvants plus Chitosan and Lignosulfonate (no polyelectrolyte binding) plus Natamycin
9) Adjuvants plus Ca-lignosulfonate plus natamycin
10) Adjuvants plus chitosan plus natamycin All treatment compositions are presented in table 4. All numbers express g/L

TABLE 4

| Formulation (g/L): | Treatment: | #1 | #2 | #3 | #4 | #5 | #6 | #7 | #8 | #9 | #10 |
|---|---|---|---|---|---|---|---|---|---|---|---|
| Water | | 664 | 664 | 664 | 664 | 664 | 664 | 664 | 664 | 664 | 664 |
| Ca-LS | | xx | 250 | 250 | 250 | xx | xx | 250 | 250 | 250 | xx |
| Chitosan | | xx | 10 | 10 | xx | 10 | xx | 10 | 10 | xx | 10 |
| H3PO3 | | xx | 5 | xx | 5 | 5 | xx | 5 | xx | 5 | 5 |
| Sodiumdioctylsuccinate (50%) | | 40 | 40 | 40 | 40 | 40 | 40 | 40 | 40 | 40 | 40 |
| Sophorolipid | | 75 | 75 | 75 | 75 | 75 | 75 | 75 | 75 | 75 | 75 |
| Xanthan (2% in H2O) | | 55 | 55 | 55 | 55 | 55 | 55 | 55 | 55 | 55 | 55 |
| Surfynol 104E | | 1 | 1 | 1 | 1 | 1 | 1 | 1 | 1 | 1 | 1 |
| Natamycin (technical 95%) | | xx | xx | xx | xx | xx | 10 | 10 | 10 | 10 | 10 |

Replicates: All treatments (1-10) were performed on 5 individual pieces of fruit with 2 wounds each resulting in 10 wounds per treatment.

Observation: All wounds were inspected daily for visual symptoms of fruit rot and/or fungus growth.

Rot diameter (perpendicular) was measured at three succeeding days. The observations were ended when all wounds of the control formulations (1-5) showed maximal symptoms of fruit rot/and or fungal growth.

| | Crop: Banana | | |
|---|---|---|---|
| Active ingredient: | Average diameter (cm) of infected spot (n = 10) days after infection | | |
| Natamycin | 5 | 6 | 7 |
| Treatment 1 | 2.6 | 3.5 | 4.6 |
| Treatment 2 | 2.9 | 4.0 | 5.3 |
| Treatment 3 | 2.7 | 3.1 | 4.8 |
| Treatment 4 | 2.9 | 3.5 | 4.6 |
| Treatment 5 | 2.8 | 3.9 | 5.0 |
| Treatment 6 | 1.4 | 2.1 | 2.8 |
| Treatment 7 | 1.3 | 1.8 | 2.5 |
| Treatment 8 | 1.7 | 2.3 | 3.2 |
| Treatment 9 | 1.2 | 1.9 | 2.7 |
| Treatment 10 | 2.0 | 3.4 | 4.2 |

Conclusion Example 3

Example 3 demonstrates that neither the Adjuvants plus Ca-lignosulfonate (treatment 4), nor the Adjuvants plus chitosan (treatment 5), nor adjuvants plus Chitosan and Lignosulfonate (no polyelectrolyte binding—treatment 3), nor the adjuvants plus Chitosan Ca-Lignosulfonate complex (CitoCal—treatment 2) have antifungal properties (compare treatment 1 with treatment 2 to 5). Example 3 also demonstrates that CitoCal provides a synergistic effect to the used active ingredient (i.e. natamycin) for the prevention of *Botrytis cinerea* fruit rot on banana when applied post-harvest, whereas, incubations without CitoCal do not (compare treatment 6 with 8 to 10).

Treatment 7, in which the polyelectrolytes Chitosan and Ca-lignosulfonate are bound, results in a decrease of the *Botrytis* infection compared to incubation 8 in which the chitosan and ca-lignosulfonate are not bound. This shows the unique effect of the polyelectrolyte complex on disease development.

Example 4

Materials and Methods:
As example 3 (treatment numbers are explained in example 3), but in example 4 only treatment 1, 2, 6 and 7 were performed. Apple fruit was used instead of banana fruit.

Results Example 4

| | Crop: Apple | | |
|---|---|---|---|
| Active ingrediënt: | Average diameter (cm) of infected spot (n = 10) days after infection | | |
| Natamycine | 3 | 4 | 5 |
| Treatment 1 | 3.9 | 10 | 22 |
| Treatment 2 | 3.2 | 7.7 | 13 |
| Treatment 6 | 0.8 | 1.6 | 4.0 |
| Treatment 7 | 0.3 | 0.9 | 2.9 |

Conclusion:
Example 4 demonstrates that the polyelectrolyte bound Chitosan and Ca-lignosulfonate (treatment 7) provides a synergistic effect to the used active ingredient (i.e. natamycin) for the prevention of *Botrytis cinerea* fruit rot on apple when applied post-harvest. This shows the unique effect of the polyelectrolyte complex on disease development.

Example 5

Materials and Methods:
As example 3 (treatment numbers are explained in example 3), but in example 5 only treatment 1, 2, 6 and 7 were performed.

Results Example 5

| | Crop: Banana | | |
|---|---|---|---|
| Active ingrediënt: | Average diameter (cm) of infected spot (n = 10) days after infection | | |
| Natamycine (100 ppm) | 4 | 5 | 6 |
| Treatment 1 | 1.9 | 2.8 | 4.0 |
| Treatment 2 | 1.7 | 2.7 | 3.8 |
| Treatment 6 | 1.6 | 2.5 | 3.9 |
| Treatment 7 | 1.4 | 2.1 | 2.9 |

Conclusion Example 5

Example 5 demonstrates that the polyelectrolyte bound Chitosan and Ca-lignosulfonate provides a synergistic effect to the used active ingredient (i.e. natamycin) for the prevention of *Botrytis cinerea* fruit rot on banana when applied post-harvest. This shows the unique effect of the polyelectrolyte complex on disease development.

Example 6

Material and Methods:
As example 3 (treatment numbers are explained in example 3), except that the tested crop is tomato fruit of organic origin and the tested formulations were diluted 200 times instead of 100 times.

Results Example 6

| | Tomato | |
|---|---|---|
| Product: | Average diameter (cm) of infected spot (n = 10) days after infection | |
| Natamycin | 3 | 4 |
| Treatment 1 | 2.7 | 4.3 |
| Treatment 2 | 2.8 | 4.3 |
| Treatment 6 | 2.4 | 3.9 |
| Treatment 7 | 1.5 | 3.4 |

Example 6 demonstrates that the polyelectrolyte bound Chitosan and Ca-lignosulfonate provides a synergistic effect to the used active ingredient (i.e. natamycin) for the prevention of *Botrytis cinerea* fruit rot on tomato when applied post-harvest. This shows the unique effect of the polyelectrolyte complex on disease development.

Example 7

Materials and Methods:
Method as in Example 3, except that the active ingredient is imazalil instead of natamycin and the polyelectrolyte of Ca-lignosulfonate and chitosan was added separately (as a 'tank mix') before spraying.
Treatments:
Treatment 1: 4 g/L Adjuvants (control); see table 5.
Treatment 2: 4 g/L Adjuvants plus 8 g/L Chitosan Ca-Lignosulfonate complex (CitoCaL); see table 5 and 6.
Treatment 3: 4 g/L Imazalil; see table 7.
Treatment 4: 4 g/L Imazalil plus 8 g/L Chitosan Ca-Lignosulfonate complex (CitoCaL); see table 6 and 7.
Formulations:

TABLE 5

| Adjuvants formulation: | |
|---|---|
| Methyloleaat | 7.53 g |
| Ethanolamine | 2.5 g |
| amine alkylbenzenesulfonate | 15.12 g |
| Sophorolipide | 6.00 g |
| polyoxyethylene sorbitol oleate | 9.02 g |
| Water | 62.38 g |

TABLE 6

| Chitosan Ca-Ligninsulfonate complex (CitoCaL) formulation: | |
| --- | --- |
| Calciumligninsulfonaat | 250.00 |
| Chitosan | 10.00 |
| H3PO3 | 5.00 |
| NaOH 35% | 13.30 |
| Sophorolipide | 75.00 |
| Surfynol 104E | 1.00 |
| Xanthan | 1.10 |
| sodiumdioctylsulfosuccinate | 40.00 |
| Water | 704.60 |

TABLE 7

| Imazalil formulation: | |
| --- | --- |
| Imazalil 97% | 10.3 g |
| Methyloleaat | 7.53 g |
| Ethanolamine | 2.5 g |
| amine alkylbenzenesulfonate | 15.12 g |
| Sophorolipide | 6.00 g |
| polyoxyethylene sorbitol oleate | 9.02 g |
| Water | 51.98 g |

Results Example 7

| | Crop: Apple | | |
| --- | --- | --- | --- |
| Active ingrediënt: | Average diameter (cm) of infected spot (n = 10) days after infection | | |
| Imazalil | 4 | 5 | 6 |
| Treatment 1 | 2.8 | 3.4 | 5.3 |
| Treatment 2 | 2.9 | 4.2 | 5.1 |
| Treatment 3 | 2.4 | 3.6 | 4.6 |
| Treatment 4 | 1.0 | 2.0 | 3.1 |

Example 7 demonstrates that the polyelectrolyte bound Chitosan and Ca-lignosulfonate provides a synergistic effect to the used active ingredient (i.e. imazalil) for the prevention of *Botrytis cinerea* fruit rot on apple when applied post-harvest. This shows the unique effect of the polyelectrolyte complex on disease development.

Example 8

Materials and Methods:
Application:

Cultivated potato plants (cv. Bintje) were grown in pots. The pots with a content of 5 liter were filled with soil and the potato tubers were placed at a depth of 10 cm. From emergence until inoculation the plants were placed outside to create short and strong stems. In the greenhouse with high temperatures the stems would be long and weak. After spraying the plants were placed in the greenhouse. Spraying was carried out when the potato plants reached a height of ~10 cm. Potato plants were sprayed in a spraying cabin developed by Applied Plant Research (PPO)—The Netherlands. The fungicides were sprayed using a spray boom with three spray nozzles, placed 50 cm apart, which was moving approximately 40 cm over the top of the potato plants. Spray volume was 250 l/ha. Potato plants were sprayed four times; on 15 May, 22 May, 31 May and 7 Jun. 2012. A *P. infestans* strain was cultivated on agar plates and potato slices. An inoculum suspension was made by rinsing a one week old culture of *P. infestans* with tap water. The inoculum density was set at approximately 10,000 sporangia per ml. Inoculation was carried out by spraying potato plants over head with approximately 8-10 ml of inoculum. Inoculation was carried out on air dry plants on 30 May 2012. After inoculation plants were incubated at a relative humidity of 100% for one night during approximately 16 hours. Disease observations were carried out 6, 9 and 12 days after inoculation. Percentage necrotic foliage per plant was estimated. Replicates: 4 replicates of 3 plants per replicate Treatments:
1) Untreated control
2) CitoCal (equivalent to 1.5 l/ha);
3) Dithane (equivalent to 2 kg/ha)
4) Dithane+CitoCal (equivalent to 2 kg/ha and 1.5 l/ha, respectively)

Formulations:

CitoCal: see example 7, table 6.

Dithane: Commercial available fungicide by Dow AgroSciences containing 75% mancozeb Results Example 8

| | Crop: Potato | | |
| --- | --- | --- | --- |
| Active ingrediënt: | Average percentage disease severity days after infection | | |
| Mancozeb | 6 | 9 | 12 |
| UTC | 37.5 | 80.3 | 87.4 |
| Citocal | 39.4 | 78.8 | 86.8 |
| Dithane | 5.0 | 9.4 | 14.9 |
| Dithane + Citocal | 2.6 | 5.1 | 11.0 |

Conclusion Example 8

Example 8 demonstrates that the polyelectrolyte bound Chitosan and Ca-lignosulfonate provides a synergistic effect to the used active ingredient (i.e. mancozeb) for the prevention of *Phytophthora infestans* late blight disease on potato when applied to whole plants. This shows the unique effect of the polyelectrolyte complex on disease development.

Example 9

Materials and Methods:

As example 8, except Shirlan was used instead of Dithane

Treatments:

1) Untreated control

2) Citocal (equivalent to 1.5 l/ha)

3) Shirlan (equivalent to 0.4 l/ha)

4) Shirlan+CitoCal (equivalent to 0.4 l/ha and 1.5 l/ha, respectively)

Formulations:

CitoCal: see example 7, table 6.

Shirlan: Commercial available fungicide by Syngenta containing 39% fluazinam

Results Example 9

| Crop: Potato | | | |
|---|---|---|---|
| Active ingredient: | Average percentage disease severity days after infection | | |
| Fluazinam | 6 | 9 | 12 |
| UTC | 37.5 | 80.3 | 87.4 |
| Citocal | 39.4 | 78.8 | 86.8 |
| Shirlan | 5.6 | 14.1 | 16.5 |
| Shirlan + Citocal | 3.4 | 7.5 | 12.3 |

Conclusion Example 9

Example 9 demonstrates that the polyelectrolyte bound Chitosan and Ca-lignosulfonate provides a synergistic effect to the used active ingredient (i.e. fluazinam) for the prevention of *Phytophthora infestans* late blight disease on potato when applied to whole plants. This shows the unique effect of the polyelectrolyte complex on disease development.

Example 10

Materials and Methods:

The cultivated grapevine plants (cv. merlot) were grown in pots. The pots were filled with potting soil and grapevine stems were planted. All stems contained 2 buds. Plants were grown outside in South West France.

Spraying was carried out when the plants had developed 4 leaves with a lance under gas pressure with an interval of 8+/−2 days until run off (equivalent of 1000 l/ha). In total, 6 plants per replicate were used, each treatment contained 3 replicates. 2 plants were artificially inoculated with 40.000 spores per ml of *Plasmopara viticola* and kept at 100% RH for 12 hours. These 2 plants served as a natural inoculum for the other 4 plants. Assessment of percentage infected leaves was done at 6, 9, 15 and 22 days after inoculation.

Treatments:
1. Commercial captan: a fungicide containing 500 g/L Captan
2. Captan formulation (containing the polyelectrolyte bound Chitosan and Ca-lignosulfonate (CitoCal)); see table 9.

TABLE 9

| Captan formulation (g/L) | |
|---|---|
| Captan techn. | 510 |
| Water (tap) | 541.3 |
| polyethoxylated fosforic acid | 40 |
| Calciumligninsulfonate | 100 |
| polydimethylsiloxane | 3 |
| Chitosan | 5 |
| Citric acid | 8 |
| NaOH techn. | 2 |
| Xanthan gum | 0.7 |
| Totals | 1210 |

Results Example 10

| Crop: Grapevine | | | | | |
|---|---|---|---|---|---|
| Active ingredient: | Dose rate | % Infected leaf area days after infection | | | |
| Captan | (L/ha) | 6 | 9 | 15 | 22 |
| UTC | — | 34 | 54 | 72 | 76 |
| Commercial captan | 0.5 | 15 | 21 | 37 | 47 |
| Captan formulation | 0.5 | 8 | 12 | 22 | 22 |
| Commercial captan | 2 | 16 | 29 | 29 | 35 |
| Captan formulation | 2 | 10 | 15 | 20 | 18 |

Summary and Conclusion:

Example 10 clearly demonstrates that the polyelectrolyte bound chitosan and Ca-lignosulfonate provides a synergistic effect to the used active ingredient (i.e. captan) for the prevention of *Plasmopara viticola*, the causal agent of downy mildew on grapevine. This shows the unique effect of the polyelectrolyte complex on disease development.

Example 11

Materials and Methods:
As example 10, however, in this experiment folpet was used instead of captan.

Treatments:
1. Commercial folpet: a fungicide containing 500 g/L folpet
2. Folpet formulation (containing polyelectrolyte bound Chitosan and Ca-lignosulfonate (CitoCal)); see table 10.

TABLE 10

| Folpet formulation (g/L): | |
|---|---|
| Folpet techn. | 510 |
| Water (tap) | 536.3 |
| polyethoxylated fosforic acid | 40 |
| Calciumligninsulfonate | 100 |
| polydimethylsiloxane | 3 |
| Chitosan | 5 |
| Fumaarzuur | 3 |
| NaOH techn. | 2 |
| Xanthan gum | 0.7 |
| Total | 1200 |

Results Example 11

| Crop: Grapevine | | | | | |
|---|---|---|---|---|---|
| Active ingredient: | Dose rate | % Infected leaf area days after infection | | | |
| Folpet | (L/ha) | 6 | 9 | 15 | 22 |
| UTC | — | 34 | 54 | 72 | 76 |
| Commercial captan | 0.5 | 17 | 39 | 45 | 44 |
| Folpet + CitoCal | 0.5 | 12 | 27 | 28 | 27 |
| Commercial captan | 2 | 10 | 36 | 27 | 35 |
| Folpet + CitoCal | 2 | 3 | 17 | 13 | 15 |

Summary and Conclusion:

Example 11 clearly demonstrates that the polyelectrolyte bound Chitosan and Ca-lignosulfonate provides a synergistic effect to the used active ingredient (i.e. folpet) for the prevention of *Plasmopara viticola*, the causal agent of downy mildew on grapevine. This shows the unique effect of the polyelectrolyte complex on disease development.

Example 12

Materials and Methods:

An open-field experiment was carried out according to the harmonised protocol according to the "European network on Potato Late Blight' in Talinn (2005), Bologna (2007), Hamar (2008) and Arras (2010). The protocol can be found on the Euroblight website (http://www.euroblight.net/Euroblight-.asp). The trial conformed to local good agricultural practice, trials were carried out in four replicates and sprays against *P. infestans* were carried out in a more or less weekly schedule.

The fungicide applications were carried out using a AZO field sprayer with 6 XR TeeJet 80015Vs nozzles approximately 50 em above the foliage. Spraying were carried out with 300 l/ha. Potato plants were sprayed for the first time at 100% emergence. Fungicides were sprayed in a weekly scheme, according to the agreed protocol. Dose was 2.0 kg/ha Dithane DG (Dow AgroSciences) for the first application and 2.25 kg/ha thereafter.

CitoCal (for formulation, see example 7, table 6) was added as a tankmix at an dose equivalent of 1.5 l/ha Tested crop: Potato cv. Bintje (field grown).

Pathogen: Natural occurring *Phytophthora infestans*

Treatments:

1) Dithane (equivalent to 2.0-2.25 kg/ha)
2) Dithane+CitoCal (equivalent to 2.0-2.25 kg/ha and 1.5 l/ha, respectively)

Observation: Percentage of disease severity was assessed throughout the trial. After the trial, stAUDPC48 was calculated based on late blight observations from Jul. 18, 2012 until 28 Aug. 2012.

Results Example 12

| Crop: Potato | |
|---|---|
|  | stAUDPC48 |
| Dithane | 0.84 |
| Dithane + Citocal | 0.64 |

Summary and Conclusion:

Example 12 clearly demonstrates that CitoCal provides a synergistic effect to the used active ingredient (i.e. mancozeb) for the prevention of *Phytophthora infestans*, the causal agent of late blight on field-grown potato.

Example 13

Materials and Methods:

The experiment was performed with a similar setup as in example 10. *Unicula necator*, the causal agent of powdery mildew on grapevine, was used instead of *Plasmopara viticola*.

Observation: Assessment of percentage infected leaves at 6, 11, 19, 28 and 42 days after inoculation Formulation:

TABLE 11

Sulfur with and without polyelectrolyte of Ca-lignosulfonate and chitosan (CitoCal) (in g/L)

|  | Sulfur + CitoCal | Sulfur − CitoCal |
|---|---|---|
| 80% sulfur | 800.00 | 800.00 |
| Water | 627.50 | 666.50 |
| Chitosan | 5.00 | — |
| HCL 37% | 2.50 | — |
| Na-LS 50% | 70.00 | 70.00 |
| polydimethylsiloxane | 5.00 | 5.00 |

Results Example 13

| Crop: Grapevine Active ingredient: | Dose rate (kg/ha elementals) | % Infected leaf area days after infection | | | | |
|---|---|---|---|---|---|---|
|  |  | 6 | 11 | 19 | 28 | 42 |
| UTC | — | 40 | 86.3 | 100 | 100 | 100 |
| Sulfur − CitoCal | 1.5 | 7.5 | 6.3 | 2.5 | 18.8 | 16.3 |
| Sulfur + CitoCal | 1.5 | 2.5 | 6.3 | 1.3 | 7.5 | 11.3 |

Summary and Conclusion:

Example 13 clearly demonstrates that CitoCal provides a synergistic effect to the used active ingredient (i.e. sulfur) for the prevention of *Uncinula necator*, the causal agent of powdery mildew on grapevine when applied to whole plants.

Examples 14, 15, 16 and 17

General.

In these experiments, we show that not only polyelectrolyte combinations of chitosan and lignosulfonate are effective in enhancement of fungicidal efficacy but also polyelectrolyte combinations of other polyanion molecules (humic acid and the synthetic compound Morwet) in combination with chitosan. In example 14 the polyelectrolyte combination is lignosulfonate-chitosan; in example 15 humic acid-chitosan and in example 16 Morwet-chitosan. In example 17, a polyelectrolyte combination of lignosulfonate and oligo-chitosan was tested on tomato fruit.

Materials and Methods:

The used protocol was based on: Dik et al., 1999. Europ J Plant Path 105: p 115-122.

Briefly, main stems of 9 individual about 50 cm tall tomato plants were cut in to 3-4 cm pieces, and randomized. Stem pieces were placed in glass reaction-tube (in a tube rack), partially filled with glass beads so 1-2 cm stem would raise above the top. All treatments were performed on 8 individual stem pieces.

Stem pieces were sprayed with $10^5$ spores/ml suspension of a freshly grown *Botrytis cinerea* culture. Subsequently, stem pieces were allowed to dry for 30 minutes.

Different formulations were prepared by adding 0.75 gram of formulation (see table 12) to 100 ml water, resulting in approx. 75 ppm natamycin (equivalent) per formulation. Stem parts were thoroughly sprayed from all directions, and placed in a carton box containing a wet towel. For high humidity, a semi-transparent bag was placed over the carton box.

Boxes with stem pieces were kept at room temperature (~19° C.) and checked frequently for *Botrytis* growth . . . .

Formulations:

TABLE 12

| Treatment: | #1 Adjuvants | #2 Adjuvants + citocal | #3 Adjuvants + CitocalHumic | #4 Adjuvants + CitocalMorwet | #5 Adjuvants + oligo-Citocal | #6 Adjuvants + ai | #7 Adjuvants + citocal + ai | #8 Adjuvants + CitocalHumic + ai | #9 Adjuvants + CitocalMorwet + ai | #10 Adjuvants + oligo-Citocal + ai |
|---|---|---|---|---|---|---|---|---|---|---|
| Water | 664 | 664 | 664 | 664 | 664 | 664 | 664 | 664 | 664 | 664 |
| Ca-Lignosulfonate | xx | 250 | | | 250 | xx | 250 | | | 250 |
| Potassium humate | | | 100 | | | | | 100 | | |
| Morwet (Akzo) | | | | 83.3 | | | | | 83.3 | |
| Chitosan | xx | 10 | 10 | 10 | | xx | 10 | 10 | 10 | |
| Oligomers of Chitosan | | | | | 10 | | | | | 10 |
| H3PO3 | xx | 5 | 5 | 5 | 5 | xx | 5 | 5 | 5 | 5 |
| Sodium-dioctylsuccinate (50%) | 40 | 40 | 40 | 40 | 40 | 40 | 40 | 40 | 40 | 40 |
| Sophorolipid | 75 | 75 | 75 | 75 | 75 | 75 | 75 | 75 | 75 | 75 |
| Xanthan gum (2% in H2O) | 55 | 55 | 55 | 55 | 55 | 55 | 55 | 55 | 55 | 55 |
| polydimethyl-siloxane | 1 | 1 | 1 | 1 | 1 | 1 | 1 | 1 | 1 | 1 |
| Natamycin | xx | xx | xx | xx | xx | 10 | 10 | 10 | 10 | 10 |

Active ingredient (A.I.) = natamycin

Assessment:

Stem pieces were scored for disease incidence:

1=less than ½ of the stem piece infected

2=½-¾ of the stem piece infected

3=¾-full infection

4=full infection

Disease incidence was calculated with the formula as described in Dik et. al. 1999. A higher number relates to a higher infection rate.

Results Example 14

See table 12 for formulation composition

| | Tomato plant (stems) | | |
|---|---|---|---|
| | Days post infection | | |
| | 7 | 8 | 9 |
| Treatment 1 (Adjuvants) | 2,500 | 3,500 | 3,750 |
| Treatment 2 (Adjuvants + CitoCal) | 2,875 | 3,125 | 3,375 |
| Treatment 6 (Adjuvants + ai) | 2,300 | 2,625 | 2,875 |
| Treatment 7 (Adjuvants + CitoCal + ai) | 2,286 | 2,571 | 2,429 |

Summary and Conclusion:

Example 14 clearly demonstrates that CitoCal provides a synergistic effect to the used active ingredient (i.e. natamycin) for the prevention of *Botrytis cinerea* stem rot on tomato plants (stem parts).

Results Example 15

See table 12 for formulation composition

| | Tomato plant (stems) | | |
|---|---|---|---|
| | Days post infection | | |
| | 7 | 8 | 9 |
| Treatment 1 (Adjuvants) | 2,500 | 3,500 | 3,750 |
| Treatment 3 (Adjuvants + humic acid-cal) | 2,500 | 2,750 | 3,125 |
| Treatment 6 (Adjuvants + ai) | 2,300 | 2,625 | 2,875 |
| Treatment 8 (Adjuvants + Humic-acid-cal + ai) | 2,167 | 2,286 | 2,125 |

Summary and Conclusion:

Example 15 clearly demonstrates that that polyelectrolyte complex of humic acid and chitosan (Humic acid-cal) provides a synergistic effect to the used active ingredient (i.e. natamycin) for the prevention of *Botrytis cinerea* stem rot on tomato.

Results Example 16

See table 12 for formulation composition.

TABLE 12

| | Tomato plant (stems) | | |
|---|---|---|---|
| | Days post infection | | |
| | 7 | 8 | 9 |
| Treatment 1 (Adjuvants) | 2,500 | 3,500 | 3,750 |
| Treatment 4 (Adjuvants + morwett-cal) | 2,750 | 3,375 | 3,375 |
| Treatment 6 (Adjuvants + ai) | 2,300 | 2,625 | 2,875 |
| Treatment 9 (Adjuvants + morwett-cal + ai) | 2,286 | 2,429 | 2,625 |

Summary and Conclusion:

Example 16 clearly demonstrates that that polyelectrolyte complex of morwet and chitosan (morwet-cal) provides a synergistic effect to the used active ingredient (i.e. natamycin) for the prevention of *Botrytis cinerea* stem rot on tomato.

Example 17

Materials and Methods:
As described in example 3, except tomato fruits were used instead of banana fruit.
Formulations:
As in example 14 (see table 12)

Results Example 17

| Crop: tomato fruit | | | |
|---|---|---|---|
| Active ingrediënt: | Average diameter (cm) of infected spot (n = 10) days after infection | | |
| natamycin | 3 | 4 | 5 |
| Adjuvants | 1 | 2.3 | 3.2 |
| Adjuvants + oligo-Citocal | 0.8 | 1.9 | 2.8 |
| Adjuvants + ai | 1 | 1.9 | 2.9 |
| Adjuvants + oligo-Citocal + ai | 0.7 | 1.6 | 2.5 |

Summary and Conclusion:
Example 17 clearly demonstrates that the combination of lignosulfonate and oligo-chitosan provides a synergistic effect to the used active ingredient (i.e. natamycin) for the prevention of *Botrytis cinerea* fruit rot on tomato fruit.

Example 18

Method:
As in example 3, except apple fruit was used instead of banana fruit. The used formulations are:
Formulations:

TABLE 13

| | Formulations (g/L) | | | |
|---|---|---|---|---|
| | Adjuvants g/L | Adjuvants + Citocal g/L | Adjuvants + Citocal + natamycin g/L | Adjuvants + natamycin g/L |
| water | 882.6 | 830.0 | 789.4 | 836.8 |
| chitosan | | 10.1 | 9.6 | |
| HCl (37%) | | 5.0 | 4.8 | |
| Calciumlignin-sulfonate | | 50.4 | 48.0 | |
| NaOH(aq) | | | | |
| mono-propyleenglycol | 71.5 | 67.2 | 64.0 | 67.8 |

TABLE 13-continued

| | Formulations (g/L) | | | |
|---|---|---|---|---|
| | Adjuvants g/L | Adjuvants + Citocal g/L | Adjuvants + Citocal + natamycin g/L | Adjuvants + natamycin g/L |
| poly-dimethylsiloxane | 7.2 | 6.7 | 6.4 | 6.8 |
| Atlox 4894 | 35.8 | 33.6 | 32.0 | 33.9 |
| Atlox 4913 | 18.6 | 17.5 | 16.6 | 17.6 |
| poly-vinylpyrrolidone (30%) | 5.7 | 5.4 | 5.1 | 5.4 |
| Natamycin (95%) | | | 53.8 | 57.1 |
| Xanthan gum (2%) | 78.7 | 74.0 | 70.3 | 74.6 |

| Crop: Apple fruits | | | |
|---|---|---|---|
| Active ingrediënt: | Average diameter (cm) of infected spot (n = 10) days after infection | | |
| Natamycin (100 ppm) | 3 | 4 | 5 |
| Adjuvants | 2.9 | 3.6 | 4.8 |
| Adjuvants + Citocal | 2.8 | 3.8 | 4.7 |
| Adjuvants + natamycin | 2.4 | 3.6 | 4.6 |
| Adjuvants + Citocal + natamycin | 1.7 | 2.6 | 3.6 |

Conclusion Example 18

Example 18 clearly demonstrates that CitoCal has no antifungal properties. Example 17 also clearly demonstrates that CitoCal provides a synergistic effect to the used active ingredient (i.e. natamycin) for the prevention of *Botrytis cinerea* fruit rot on apple when applied post-harvest.

Example 19

We show in this experiment the efficacy of the different polyelectrolytes on (apple) fruits.
Method:
Material and methods are as in example 3, except apple fruit was used instead of banana fruit.
Treatments:
1=Adjuvanits
2=Adjuvants+citocal
3=Adjuvants+CitocaiHumicAcid
4=Adjuvants+CitocalMorwet
5=Adjuvants+oligo-Citocal
6=Adjuvants+folpet
7=Adjuvants+citocal+folpet
8=Adjuvants+CitocaiHumic+folpet
9=Adjuvants+CitocalMorwet+folpet
10=Adjuvants+oligo-Citocal+folpet
Formulations:

TABLE 14

| | Formulation (g/L): | | | | | | | | | |
|---|---|---|---|---|---|---|---|---|---|---|
| Treatments | #1 Adjuvants | #2 Adjuvants + citocal | #3 Adjuvants + CitocalHumic | #4 Adjuvants + CitocalMorwet | #5 Adjuvants + oligo-Citocal | #6 Adjuvants + ai | #7 Adjuvants + citocal + ai | #8 Adjuvants + CitocalHumic + ai | #9 Adjuvants + CitocalMorwet + ai | #10 Adjuvants + oligo-Citocal + ai |
| Water | 528.5 | 528.5 | 528.5 | 528.5 | 528.5 | 528.5 | 528.5 | 528.5 | 528.5 | 528.5 |
| Ca-LS | | 35.0 | | | 35.0 | | 35.0 | | | 35.0 |
| KHumaat | | | 35.0 | | | | | 35.0 | | |

TABLE 14-continued

| Treatments | #1 Adjuvants | #2 Adjuvants + citocal | #3 Adjuvants + CitocalHumic | #4 Adjuvants + CitocalMorwet | #5 Adjuvants + oligo-Citocal | #6 Adjuvants + ai | #7 Adjuvants + citocal + ai | #8 Adjuvants + CitocalHumic + ai | #9 Adjuvants + CitocalMorwet + ai | #10 Adjuvants + oligo-Citocal + ai |
|---|---|---|---|---|---|---|---|---|---|---|
| Morwet D425 | | | | 35.0 | | | | | 35.0 | |
| Chitosan | | 5.0 | 5.0 | 5.0 | | | 5.0 | 5.0 | 5.0 | |
| Chs oligo | | | | | 5.0 | | | | | 5.0 |
| Fumaric acid | 29.0 | 29.0 | 29.0 | 29.0 | 29.0 | 29.0 | 29.0 | 29.0 | 29.0 | 29.0 |
| NaOH | 20.0 | 20.0 | 20.0 | 20.0 | 20.0 | 20.0 | 20.0 | 20.0 | 20.0 | 20.0 |
| Sophrophor FL | 40.0 | 40.0 | 40.0 | 40.0 | 40.0 | 40.0 | 40.0 | 40.0 | 40.0 | 40.0 |
| ATLOX 4913 | 40.0 | 40.0 | 40.0 | 40.0 | 40.0 | 40.0 | 40.0 | 40.0 | 40.0 | 40.0 |
| Xanthan opl | 37.5 | 37.5 | 37.5 | 37.5 | 37.5 | 37.5 | 37.5 | 37.5 | 37.5 | 37.5 |
| polydimethyl-siloxane | 5.0 | 5.0 | 5.0 | 5.0 | 5.0 | 5.0 | 5.0 | 5.0 | 5.0 | 5.0 |
| Folpet techn. | | | | | | 510.0 | 510.0 | 510.0 | 510.0 | 510.0 |
| Totals | 700.0 | 740.0 | 740.0 | 740.0 | 740.0 | 1210.0 | 1250.0 | 1250.0 | 1250.0 | 1250.0 |

Results Example 19

| | Crop: Apple fruit |
|---|---|
| Active ingredient: Folpet (1 g/L) | Average diameter (cm) of infected spot (n = 10) days after infection 4 |
| Treatment 1 (Adjuvants) | 2.2 |
| Treatment 2 (Adjuvants + Citocal) | 2.4 |
| Treatment 3 (Adjuvants + CitocalHumicAcid) | 2.5 |
| Treatment 4 (Adjuvants + CitocalMorwet) | 2.6 |
| Treatment 5 (Adjuvants + oligo-Citocal) | 2.3 |
| Treatment 6 (Adjuvants + folpet) | 1.5 |
| Treatment 7 (Adjuvants + Citocal + folpet) | 1.2 |
| Treatment 8 (Adjuvants + CitocalHumic + folpet) | 1.2 |
| Treatment 9 (Adjuvants + CitocalMorwet + folpet) | 1.3 |
| Treatment 10 (Adjuvants + oligo-Citocal + folpet) | 1.1 |

Conclusions Example 19

Example 19 clearly demonstrates that none of the polyelectrolytes have antifungal properties. Example 19 also demonstrates that different polyelectrolyte complexes provide a synergistic effect to the used active ingredient (i.e. folpet) for the prevention of *Botrytis cinerea* on apple when applied post-harvest.

Example 20

Method:

As example 14, except formulations as in example 18; see table 13.

Results:

| | Crop: Tomato plant (stems) | | |
|---|---|---|---|
| | dpi | | |
| | 7 | 8 | 9 |
| Adjuvants | 3.2 | 3.6 | 3.9 |
| Adjuvants + CitoCal | 3.3 | 3.5 | 3.9 |
| Adjuvants + natamycin | 3.1 | 3.6 | 3.9 |
| Adjuvants + CitoCal + natamycin | 2.6 | 2.8 | 3 |

Conclusion Example 20

Example 20 clearly demonstrates that CitoCal provides a synergistic effect to the used active ingredient (i.e. natamycin) for the prevention of *Botrytis cinerea* stem rot on tomato. Example also clearly demonstrates that CitoCal has no antifungal properties by itself.

Example 21

Formation of Chitosan-Lignosulfonate Polyelectrolyte Complex:

The following experiments is a repeat of the experiments described in the Pakistan Journal of Biological Sciences 11 (19); 2291-2299, 2008.

Chitosan (3 gr) was added to 100 mL of water containing 1% acetic acid. The semi-clear solution was stirred. Than 1% solution of Calcium-lignosulfonate in 100 mL water was added to the chitosan solution. This resulted in a milky solution. No precipitation of solids was observed. Furthermore, if this solution was diluted with water no precipitation was observed.

Example 22

10 gram of Chitosan was suspended in 885 mL water, 5 gram 37% HCl was added to completely dissolve the chitosan. Then 100 grain Calcium-Lignosulfonate was added portion wise to the solution. A milky solution appeared immediately and solids precipitated from the solution. When a further 40-50 grams of the Ca-LS was added a rise in viscosity was observed and the aqueous solution thickened and the polyelectrolyte clearly separated as a solid from the aqueous phase. By addition of the remaining 50 gr Ca-LS the aqueous phase became less viscous. The solid was settled overnight and filtered over a Buchner funnel. The filter was washed several times to remove the excess water soluble Ca-LS. The solid was dried in order to measure the weight of the reaction product. The weight of the solid after drying was 62.4 gram. 10 grams of this complex is chitosan, this means that slightly more than 50 grams is Lignosulfonate. The ratio Chitosan:Ca-LS is therefore about 1:5 (w/w).

Example 23

When the same experiment as in example 22 was performed with 20 gram chitosan in 500 mL water (more concentrated), the viscosity was raised dramatically and the resulting jelly solution was hardly stirrable after addition of 35 gram Ca-LS. However, after an additional 125 grams of Ca-LS the aqueous phase became less viscous. The solid was settled overnight and filtered over a Buchner funnel. The filter was washed several times to remove the excess water soluble Ca-LS. The solid was dried in order to measure the weight of the reaction product. The ratio was determined as described above and appeared to be Chitosan:-Ca-LS 1:3.

CONCLUSION

The complex formed in experiment 20 mainly contained protonated chitosan and therefore remained in solution. The complex formed in experiment 23 contained less lignosulfonate because the partly formed complex already precipitated from the aqueous phase before the whole neutral complex was formed. Clearly not enough water was available to keep the protonated chitosan amine groups in solution and therefore prevented the reaction with the excess Ca-Lignosulfonate to completion. In experiment 22 enough water was available to completely form the whole neutral chitosan-lignosulfonate polyelectrolyte complex.

The invention claimed is:

1. A composition comprising a solid, insoluble bound polyelectrolyte complex of a polyanion and a polycation comprising chitosan or a chitosan oligosaccharide, wherein said polyanion and said polycation are present in relative amounts of from 2:1 to 30:1 (w/w), said composition further comprising at least one biocide, wherein said polyelectrolyte complex provides a synergistic effect to said biocide.

2. The composition of claim 1, wherein said polyanion is selected from the group consisting of xanthan gum, humic acid, alginate and lignosulfonate.

3. The composition of claim 1, wherein said polycation is or comprises chitosan.

4. The composition according to anyone of claims 1-3, wherein said biocide is present in a concentration of between 0.1 and 90 w/v %.

5. The composition of claim 1, wherein said polyanion and polycation are present in relative amounts of about 5:1 (w/w).

6. The composition of claim 1, wherein the biocide is a fungicide.

7. The composition of claim 1, comprising a polyelectrolyte complex of a polyanion and a polycation and at least one biocide, wherein the composition is a suspension concentrate.

8. The composition of claim 1, comprising a polyelectrolyte complex of a polyanion and a polycation and at least one biocide, wherein the composition is a water dispersible granule.

9. The composition of claim 1, wherein the polyanion comprises a natural polyanion.

10. The composition of claim 9, wherein the natural polyanion comprises at least one of xanthan gum, alginate, a lignin compound such as lignosulfonate, pectin, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate and hyaluronic acid.

11. The composition of claim 1, wherein the polyanion is a synthetic polyanion.

12. The composition of claim 11, wherein the synthetic polyanion comprises at least one of poly(acrylic acid), polyphosphoric acid, and poly(L-lactide).

13. The composition of claim 1, wherein the polycation comprises at least one of poly-L-lysine, epsilon-poly-L-lysine, poly-L-arginine, chitosan oligosaccharide and chitosan.

14. A method for generating a composition according to any one of claims 1-3, 4-8, comprising
(a) providing an aqueous solution of a polyanion, wherein the concentration of polyanion is 1-20% (w/v);
(b) providing an acidic solution of a polycation, wherein the concentration of the polycation is 1-10% (w/v) and the pH is below pH=5.5;
(c) adding the polyanion solution to the polycation solution, wherein said polyanion and polycation are present in relative amounts of from 2:1 to 30:1 (w/w), whereby a formed precipitate is crushed; and
(d) adding a biocide to the solution of at least one of steps a-c.

15. The method according to claim 14, wherein said polyanion is selected from the group consisting of xanthan gum, alginate and lignosulfonate.

16. The method according to claim 14, wherein said polycation is or comprises chitosan.

17. The method according to claim 14, wherein the acidic polycation solution comprises lactate, hydrochloric acid, and/or ascorbic acid.

18. A method of protecting an agricultural plant against a pathogen, comprising applying to said agricultural plant or to one or more plant parts a composition according to claim 1.

19. A method of preventing, reducing and/or eliminating the presence of a pathogen on a plant or to one or more plant parts, comprising applying to said plant or plant part a composition according to claim 1.

20. The method of claim 19, wherein the pathogen is *Botrytis*.

21. The method of claim 19, wherein the plant part comprises seed, leaf or fruit.

22. The method of any one of claims 18-21, wherein the plant part is a post-harvest fruit.

23. The method according to claim 14, wherein the polyanion comprises a natural polyanion.

24. The method of claim 23, wherein the natural polyanion comprises at least one of xanthan gum, alginate, a lignin compound such as lignosulfonate, pectin, carrageenan, humic acid, fulvic acid, angico gum, gum Kondagogu, sodium alkyl naphtalene sulfonate, poly-γ-glutamic acid, maleic starch half-ester, carboxymethyl cellulose, chondroitin sulphate, dextran sulphate and hyaluronic acid.

25. The method of claim 14, wherein the polyanion is a synthetic polyanion.

26. The method of claim 25, wherein the synthetic polyanion comprises at least one of poly(acrylic acid), polyphosphoric acid, and poly(L-lactide).

27. The method of claim 14, wherein the polycation comprises at least one of poly-L-lysine, epsilon-poly-L-lysine, poly-L-arginine, chitosan oligosaccharide and chitosan.

* * * * *